United States Patent
Yang et al.

(10) Patent No.: US 10,150,742 B2
(45) Date of Patent: Dec. 11, 2018

(54) SUBSTITUTED HETEROCYCLIC COMPOUNDS FOR TREATING OR PREVENTING VIRAL INFECTIONS

(71) Applicants: President and Fellows of Harvard College, Cambridge, MA (US); Dana-Farber Cancer Institute, Inc., Boston, MA (US)

(72) Inventors: Priscilla Yang, Boston, MA (US); Nathanael S. Gray, Boston, MA (US); Chandrasekhar Miduturu, Cambridge, MA (US); Margaret J. Clark, Zurich (CH)

(73) Assignees: President and Fellows of Harvard College, Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 14/777,109

(22) PCT Filed: Mar. 14, 2014

(86) PCT No.: PCT/US2014/027654
§ 371 (c)(1),
(2) Date: Sep. 15, 2015

(87) PCT Pub. No.: WO2014/152716
PCT Pub. Date: Sep. 25, 2014

(65) Prior Publication Data
US 2016/0031826 A1  Feb. 4, 2016

Related U.S. Application Data

(60) Provisional application No. 61/787,956, filed on Mar. 15, 2013.

(51) Int. Cl.
| | | |
|---|---|---|
| *C07D 239/42* | (2006.01) | |
| *C07D 239/47* | (2006.01) | |
| *C07D 239/48* | (2006.01) | |
| *C07D 239/69* | (2006.01) | |
| *C07D 403/04* | (2006.01) | |
| *C07D 413/14* | (2006.01) | |
| *C07D 417/14* | (2006.01) | |

(52) U.S. Cl.
CPC ......... *C07D 239/42* (2013.01); *C07D 239/47* (2013.01); *C07D 239/48* (2013.01); *C07D 239/69* (2013.01); *C07D 403/04* (2013.01); *C07D 413/14* (2013.01); *C07D 417/14* (2013.01)

(58) Field of Classification Search
CPC .. C07D 239/42; C07D 239/47; C07D 239/48; C07D 239/69; C07D 403/04; C07D 413/14; C07D 417/14
See application file for complete search history.

(56) References Cited

U.S. PATENT DOCUMENTS

| | | | |
|---|---|---|---|
| 6,235,746 B1 | 5/2001 | Davis et al. | |
| 6,939,874 B2 | 9/2005 | Harmange et al. | |
| 7,435,814 B2* | 10/2008 | Singh | A61K 31/519 544/105 |
| 2005/0014753 A1* | 1/2005 | Ding | C07D 239/42 514/241 |
| 2010/0152182 A1 | 6/2010 | Baenteli et al. | |
| 2010/0197918 A1 | 8/2010 | Singh et al. | |
| 2011/0312908 A1* | 12/2011 | Gray | C07D 239/42 514/46 |

FOREIGN PATENT DOCUMENTS

WO    WO-2009/073153 A2    6/2009

OTHER PUBLICATIONS

Lawrence et al., Journal of Medicinal Chemistry, 7392-7416, 55, 2012.*
Registry No. 724431-60-1, File Registry on STN, Aug. 9, 2004.*
International Search Report dated Jul. 21, 2014, from PCT/US14/27654.
Clark, Margaret Jean, "Exploring Dengue Virus Entry through Small Molecule Inhibition and Mutagenesis of the Envelope Protein," Doctoral Dissertation, Harvard University (2012).
PUBCHEM CID-16044627 (created Apr. 27, 2007).

* cited by examiner

*Primary Examiner* — Rebecca L Anderson
(74) *Attorney, Agent, or Firm* — Foley Hoag LLP

(57) ABSTRACT

Disclosed herein are pyrimidine compounds of formula I and formula II and methods for treating or preventing a viral infection, such as infections caused by dengue virus in a subject, comprising administering to said subject an effective amount of a pyrimidine compound of formula I or formula II.

9 Claims, 32 Drawing Sheets

Figure 1

| Inhibitor | Src | Abl | c-Kit, PDGFR, VEGFR | Other kinase targets |
|---|---|---|---|---|
| K002 | | | | CDKs |
| K014 (Imatinib) | | X | X | |
| K039 | | | | c-Raf |
| K040 | | | | JAK1, -2, -3 |
| K003 | X | X | X | |
| K013 (GNF2) | | X | | |
| K030 | X | | | Kdr |
| K032 | | | | CK II |
| K117 | X | | | |
| K045 (AZD0530) | X | X | | |
| K005 (Dasatinib) | X | X | X | |
| K025 (SU11652) | | | X | FGFR |
| K028 (Lavendustin A) | X | | | EGFR |
| K026 (SU5271) | | | | EGFR |
| K144 (Kenpaullone) | X | | | CDKs, GSK3-b |
| K115 (Lavendustin C) | X | | | CaMK II |
| K116 (MC7) | | | | MLCK |
| K118 (Tyrphostin46) | X | X | X | Multi-targeted |

| | compound ID | R$_1$ | IC$_{90}$ (μM) | | | | LD$_{90}$ (μM) |
|---|---|---|---|---|---|---|---|
| | | | DV1 | DV2 | DV3 | DV4 | |
| X= H | CVM-07-126-2 |  | 20 uM | 25 uM | 5 uM | 40 uM | 50 uM |
| | CVM-07-148-2 |  | 20 uM | 25 uM | >40 uM | 10 uM | 80 uM |
| | CVM-07-148-6 |  | 10 uM | 25 uM | >40 uM | >40 uM | 100 uM |
| | CVM-07-127-B |  | 20 uM | 25 uM | 40 uM | >40 uM | 40 uM |
| | CVM-07-148-9 |  | 10 uM | 25 uM | >40 uM | 5 uM | 80 uM |
| | CVM-07-148-7 |  | 4 uM | 20 uM | 30 uM | >40 uM | 50 uM |
| | CVM-2-12-2 |  | 4 uM | 5 uM | 10 uM | 40 uM | 60 uM |
| | CVM-07-148-1 |  | 10 uM | 17.5 uM | >40 uM | 10 uM | 100 uM |
| | CVM-07-148-8 |  | 10 uM | 10 uM | >40 uM | 20 uM | 100 uM |
| | CVM-07-126-3 |  | 5 uM | 10 uM | >40 uM | 40 uM | 100 uM |
| | CVM-07-111-1-B |  | 40 uM | 15 uM | >40 uM | 40 uM | >100 uM |
| X= Cl | CVM-07-128-B |  | 5 uM | 15 uM | 10 uM | 10 uM | >100 uM |

| cmpd ID | R₁ | IC$_{90}$ (μM) | | | | LD$_{90}$ (μM) |
|---|---|---|---|---|---|---|
| | | DV1 | DV2 | DV3 | DV4 | |
| CVM-08-24-1 |  | 4 uM | 25 uM | >40 uM | 15 uM | 50 uM |
| CVM-08-24-5 |  | 1 uM | 25 uM | >40 uM | 15 uM | 90 uM |
| CVM-2-12-3 |  | 1 uM | 5 uM | 40 uM | 17.5 uM | 100 uM |
| CVM-07-119-2-B |  | 1 uM | 20 uM | >40 uM | 10 uM | 90 uM |
| CVM-08-24-2 |  | 7 uM | 17.5 uM | >40 uM | 35 uM | >100 uM |
| CVM-08-24-4 |  | 3 uM | 7.5 uM | 40 uM | 7.5 uM | 75 uM |
| CVM-08-24-3 |  | 3 uM | 5 uM | >40 uM | 10 uM | 90 uM |

Figure 19

| cmpd ID | R₁ | p.f.u/mL at 75 μM | Log units decrease of p.f.u rel to DMSO | IC$_{90}$ (μM) | | | | LD$_{90}$ (μM) |
|---|---|---|---|---|---|---|---|---|
| | | | | DV1 | DV2 | DV3 | DV4 | |
| CVM-2-12-4 | | 133 ± 115 | 0.9 | 1 uM | 20 uM | 30 uM | 5 uM | >100 uM |
| CVM-07-120 | | 13 ± 20 | 2.3 | 10 uM | 20 uM | >40 uM | 7.5 uM | 75 uM |
| CVM-2-21-2 | | 75 ± 20 | 1.1 | 3 uM | 25 uM | >40 uM | 30 uM | >100 uM |

| cmpd ID | R₁ | R₂ | IC$_{90}$ (μM) | | | | LD$_{90}$ (μM) |
|---|---|---|---|---|---|---|---|
| | | | DV1 | DV2 | DV3 | DV4 | |
| JW-124 |  |  | 10 uM | 25 uM | 30 uM | 9 uM | 25 uM |
| JW-125 |  |  | 10 uM | 25 uM | 25 uM | 5 uM | 90 uM |

| cmpd ID | R₁ | IC₉₀ (μM) | | | | LD₉₀ (μM) |
|---|---|---|---|---|---|---|
| | | DV1 | DV2 | DV3 | DV4 | |
| CVM-1-100-1 | (phenyl) | 20 uM | 7.5 uM | >40 uM | 15 uM | 40 uM |

$IC_{90}$ ~20μM

GNF-2

IC$_{90}$ 18 µM in the infectivity assay

IC$_{90}$ ~18µM c-GNF-2

IC$_{90}$ 60 μM in the infectivity assay

| JW-125 | | | |
|---|---|---|---|
| IC$_{90}$ (µM) | | | |
| DV1 | DV2 | DV3 | DV4 |
| 10 uM | 25 uM | 20 uM | 10 uM |

CVMR-24-3

IC$_{90}$ 5µM

Figure 29
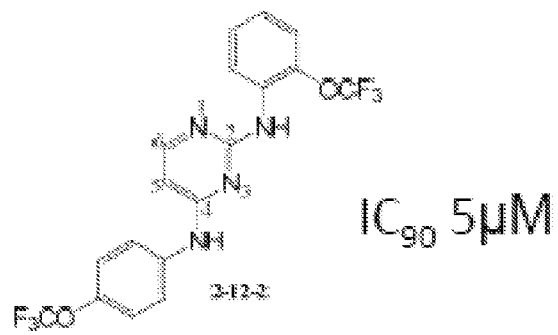
Figure 30
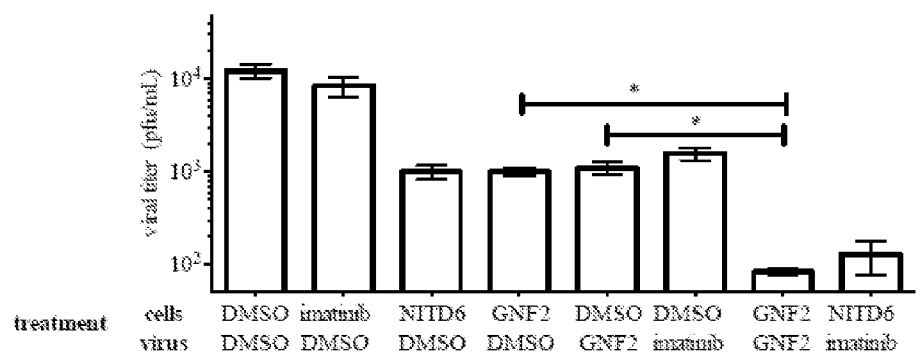
Figure 31
| Compound Number | IC50 | | | log decr. Virus 100 uM | log decr. Virus 10uM |
|---|---|---|---|---|---|
| | Ba/F3 | BCR-Abl | T315I | | |
| OB-404 | >10 | 0.77 | >10 | 1.52 | 1.05 |
| OB-413 | >10 | 0.23 | >10 | 2.52 | 1.89 |
| OB-362F | 2.3 | 0.035 | 0.6 | 1.54 | 0.82 |
| OB-341I | >10 | 0.12 | 3.47 | 2.3 | 1.59 |
| OB-361B | >10 | >10 | >10 | 1.64 | 1.15 |
| OB-364C | >10 | >10 | >10 | 1.52 | 1.05 |

| Compound | EC90 (µM) | IC50 (µM) | KD (µM) |
|---|---|---|---|
| JWF-111 | 30 | | 1.9 |
| JWF-123 | 10 | 0.8 | |
| JWF-103 | 15-20 | | 2.3 |
| JWF-129 | | 1.2 | |
| JWF-126 | 15 | | 2.2 |
| JWF-107 | 50 | | 10 |
| JWF-121 | 5 | | 1 |
| JWF-127 | 10 | | |
| GNF-2-FITC (JWD-034) | >20 | 3 | |
| JBJ-01-013 | 10 | | |
| JBJ-01-003 | 15 | | |
| JBJ-01-017 | 15 | | |
| JWF-074 | 22 | | |
| JWF-075 | 22 | | |
| JWF-084 | 10 | | |
| JWF-083 | 25 | | |
| JWF-078 | 5 | | |

SUBSTITUTED HETEROCYCLIC COMPOUNDS FOR TREATING OR PREVENTING VIRAL INFECTIONS

RELATED APPLICATIONS

This application is the U.S. National Stage application of PCT/US14/027654, filed Mar. 14, 2014, which claims the benefit of priority to U.S. Provisional Patent Application Ser. No. 61/787,956, filed Mar. 15, 2013; the contents of both of which are hereby incorporated by reference.

GOVERNMENT SUPPORT

This invention was made with government support under Grant Nos. AI057159-07 and AI095499-01 awarded by the National Institutes of Health, National Institute of Allergy and Infectious Disease. The government has certain rights in this invention.

BACKGROUND

The flavivirus family includes several clinically important animal viruses, including Dengue, West Nile, Japanese encephalitis, yellow fever, and tick-borne encephalitis viruses. Dengue is one of the most serious infectious diseases globally. There are about 300 million cases every year, with over 500,000 cases of potentially fatal Dengue hemorrhagic fever. Dengue virus (DENV) puts nearly 2.5 billion people at risk of infection in tropical and subtropical countries. Similarly, West Nile virus (WNV) has caused thousands of human infections in North America, besides infecting people on other continents. WNV infection can lead to serious illnesses in humans, resulting in encephalitis and death. Neither a prophylactic vaccine nor antiviral therapies are available for both WNV and DENV. The development of either a vaccine or an antiviral drug requires detailed knowledge of the viral life cycle.

The spherical, approximately 50 nm diameter dengue virion contains an inner nucleocapsid made up of the plus-sense RNA genome and multiple copies of the viral core protein and is sheathed in a lipid bilayer derived from the host cell. The virion membrane is coated with 180 copies of the envelope (E) protein that form 90 homodimers arranged in a tight herringbone structure. Following attachment to the cell surface, the dengue virion is internalized via a clathrin-dependent process. The viral nucleocapsid escapes from the endosomal compartment via a pore created upon fusion of the viral and endosomal membranes. This process of viral fusion is catalyzed by the E protein and is triggered by acidic pH. The viral genome is translated to produce a single polyprotein that is post-translationally processed by cellular and viral proteases to produce the ten DENV proteins. Replication of the viral genome is catalyzed by the viral RNA-dependent RNA polymerase, NS5, and occurs in membrane-associated complexes in the perinuclear region. Upon encapsidation of the viral genomic RNA by the core protein, the nucleocapsids bud into the endoplasmic reticulum lumen, a process that leads to their acquisition of a lipid membrane and association with 180 heterodimers of the viral E and prM proteins organized as quasi-trimers arranged perpendicularly to the virion surface. prM functions as a chaperone protein to prevent premature triggering of the E protein on immature viral particles within the acidic environment of the secretory pathway. Mature viral particles are produced upon cleavage of prM by furin and rearrangement of E into homodimers during exocytosis. The DENV infectious cycle is known to occur on the timescale of several hours, with the release of progeny viral particles commencing at 12 to 24 hours following infection, depending upon the virus strain and cell-type.

Based on its tertiary structure, the DENV E protein is a class II viral fusion protein. Two transmembrane domains anchor the E protein in the viral membrane and are linked to three globular domains (domains I, II, and III) via a short "stem" region and membrane proximal helix-loop-helix. Domain I is a β-barrel forming the core of the protein monomer. The immunoglobulin-like domain III acts as the putative receptor-binding domain and is the major site of neutralizing antibody epitopes. The fusion loop located at the tip of the "finger-like" domain II contacts domain III of the dimer partner. The large-scale structural changes triggered by the acidification of the endosomal compartment catalyze fusion of the viral and target membranes.

Viruses can be interrogated using chemical tools; for example, small molecules or RNAi may be used to identify host factors or pathways integral for viral replication or viral entry. Specifically, host proteins and enzymes that may be important for viral replication may be probed by measuring the effect on yield of viral particles in the presence of known inhibitors of a specific protein or enzyme. In addition, small molecules may inhibit viral entry by interacting with viral proteins, such as envelope protein E.

In general, there exists a need for antiviral therapies that are not detrimental to host cell viability.

SUMMARY

In certain embodiments, the invention relates to a compound, or a pharmaceutically acceptable salt, solvate, hydrate, prodrug, chemically-protected form, enantiomer or stereoisomer thereof, wherein the compound is represented by formula I or formula II

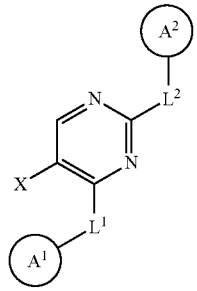

Formula I

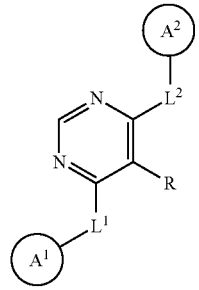

Formula II wherein, independently for each occurrence,

is optionally substituted aryl or optionally substituted heteroaryl;

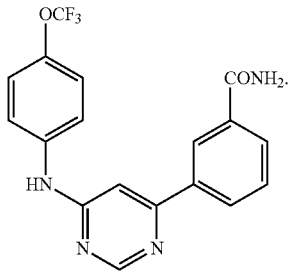

is optionally substituted aryl or optionally substituted heteroaryl;

$L^1$ is a bond, —NR—, —O—, $CR_2$—, —S—, —$(CR_2)_2$—, —C(O)—NR—, —NR—C(O)—, —C(O)O—, —O—C(O)—, —$OCR_2$—, —$CR_2O$—, —NR—$CR_2$—, or —$CR_2$—NR—;

$L^2$ is a bond, —NR—, —O—, $CR_2$—, —S—, —$(CR_2)_2$—, —C(O)—NR—, —NR—C(O)—, —C(O)O—, —O—C(O)—, —$OCR_2$—, —$CR_2O$—, —NR—$CR_2$—, or —$CR_2$—NR—;

X is H or halo; and

R is H, alkyl, aryl, or aralkyl, provided the compound is not

In certain embodiments, the invention relates to a method of inhibiting entry of a virus into a host cell comprising contacting the host cell with an effective amount of any one of the aforementioned compounds.

In certain embodiments, the invention relates to any one of the aforementioned methods, wherein the virus is dengue virus (DENV).

In certain embodiments, the invention relates to a method of treating or preventing a viral infection in a subject comprising administering to the subject, (e.g., a subject in need thereof), an effective amount of any one of the aforementioned compounds.

In certain embodiments, the invention relates to any one of the aforementioned methods, wherein the viral infection is a result of dengue virus (DENV).

BRIEF DESCRIPTION OF THE DRAWINGS

FIG. 1 depicts a screen of kinase inhibitors with anti-DENV activity. Several Abl kinase inhibitors exhibit activity against dengue virus.

FIGS. 17-21 tabulate the $IC_{90}$ and $LD_{90}$ values for various compounds of the invention. In particular, the tables demonstrate that compounds of the invention have activity against multiple serotypes of DENV. Certain compounds of the invention exhibit pan-serotype activity.

FIGS. 22-29 depict the $IC_{90}$ values associated with various compounds of the invention.

FIG. 30 depicts that GNF-2 has additive effects on DENV titer. All virus and cell treatments were done at $EC_{90}$ values determined empirically. Virus treatment was carried out for 45 minutes at 37° C. prior to initial cell infection (MOI 1). Treatment of BHK-21 cells was begun immediately after the initial one-hour infection. Each bar represents the mean of three replicates with error bars showing standard deviation. * indicates p value<0.01.

FIG. 31 tabulates the $IC_{50}$ for various 4,6-disubstituted compounds of the invention. Virus was preincubated with 10 or 100 micromolar compound. Excess compound was removed by size exclusion then used to infect cells at MOI 1. Viral yield determined at 24 h post-infection. Log 10 unit decrease indicated in columns on the right.

DETAILED DESCRIPTION

Overview

Figure 2:
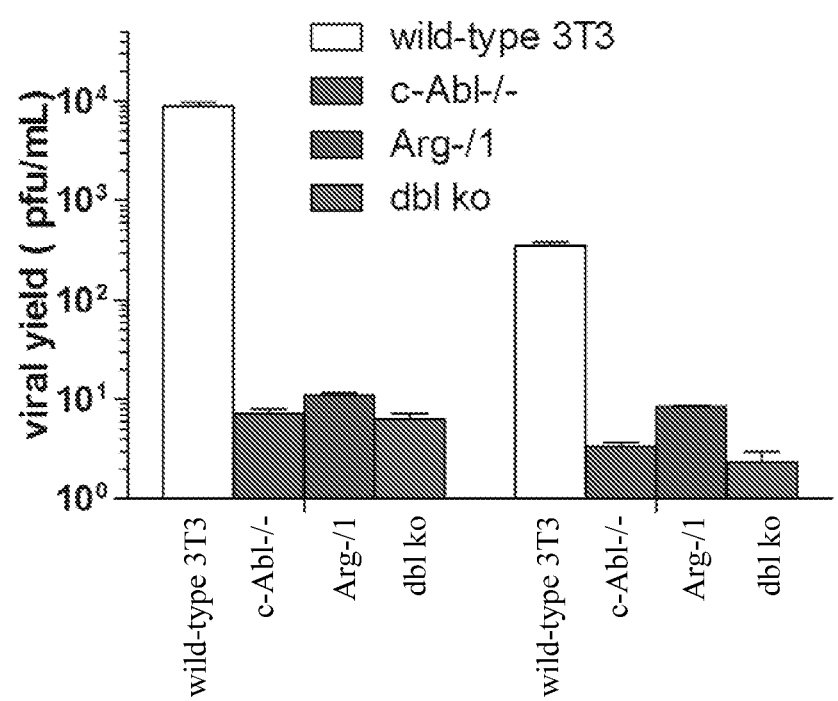
FIG. 2 depicts that DENV replication is reduced in cell lines lacking Abl kinase activity (left set of data=MOI 10; right set of data=MOI 1).

In certain embodiment, the invention relates to the effect of small molecules (compounds or active agents) on viral replication. In certain embodiments, the small molecules interact with host cell factors, such as enzymes, and so perturb viral replication. In certain embodiments, the host cell factor is a kinase. Kinases play a central role in intracellular signal transduction and regulate many cellular processes, including cell division, apoptosis, immune activation, trafficking, and cell survival. In certain embodiments, the host cell factor is a tyrosine kinase.

In certain embodiments, the compound is an inhibitor of intracellular Abl kinase. In certain embodiments, the compound blocks viral entry independent of its Abl kinase activity. In certain embodiments, the compound binds directly to a protein associated with the virion. In certain embodiments, the compound binds directly to a virion envelope protein. In certain embodiments, the compound blocks DENV fusion at a step after insertion of the fusion loops.

GNF-2, an allosteric inhibitor of the Bcr-Abl kinase and other Abl kinases, was identified as an inhibitor of the infectious cycle of DENV in cell culture. In certain embodiments, the invention relates to efforts to elucidate the mechanism by which GNF-2 inhibits DENV2. In certain embodiments, the invention relates to the discovery that GNF-2's inhibition of DENV is mediated by two distinct mechanisms, one mediated by Abl kinases and one that is independent of Abl kinases and instead mediated by the DENV E protein on the virion surface. In dose-response and order of addition experiments, GNF-2 inhibited DENV infectivity when pre-incubated with the viral inoculum; however, this inhibition could not be entirely recapitulated with imatinib, a comparably potent but structurally distinct inhibitor of Abl kinases. Employing a chemical biology approach, we synthesized derivatives of GNF-2 conjugated to biotin and FITC and then demonstrated the interaction of these compounds with purified dengue virions and recombinant proteins corresponding to the soluble prefusion dimer ($sE_2$), respectively. We furthermore performed a focused medicinal chemistry study to elucidate differences in the structure-activity relationships underlying GNF-2's kinase inhibitory activity versus those responsible for its inhibition of DENV infectivity, leading to the identification of compound 2-12-2, a 2,4-disubstituted pyrimidine that lacks cellular activity against Abl kinases but whose inhibition of DENV infectivity is improved relative to GNF-2. In certain embodiments, compound 2-12-2 blocks fusion of dengue virions with model liposomes in vitro, suggesting that its interaction with E prevents membrane fusion during DENV entry.

ABL Tyrosine Kinases and Abl Kinase Inhibitors

ABL-family proteins comprise one of the best conserved brandies of the tyrosine kinases. Each ABL protein contains an SH3-SH2-TK (Src homology 3-Src homology 2-tyrosine kinase) domain cassette, which confers autoregulated kinase activity and is common among nonreceptor tyrosine kinases. This cassette is coupled to an actin-binding and -bundling domain, which makes ABL proteins capable of connecting phosphoregulation with actin-filament reorganization. Two vertebrate paralogs, ABL1 and ABL2, have evolved to perform specialized functions. ABU includes nuclear localization signals and a DNA binding domain through which it mediates DNA damage-repair functions, whereas ABL2 has additional binding capacity for actin and for microtubules to enhance its cytoskeletal remodeling functions. Several types of posttranslational modifications control ABL catalytic activity, subcellular localization, and stability, with consequences for both cytoplasmic and nuclear ABL functions. Binding partners provide additional regulation of ABL catalytic activity, substrate specificity, and downstream signaling.

Bcr-Abl tyrosine-kinase inhibitors (TKI) are the first-line therapy for most patients with chronic myelogenous leukemia (CML). In more than 90% cases CML is caused by chromosomal abnormality resulting in the formation of a so-called Philadelphia chromosome. Compounds have been developed that selectively inhibit this tyrosine kinase. Before the U.S. Food and Drug Administration (FDA) approval of imatinib in 2001 no drugs were used that changed the natural progression of CML, only cytotoxic drugs such as busulfan, hydroxyurea or interferon-alpha (rIFN-α). Most of the drugs are adenosine triphosphate (ATP)-competitive inhibitors.

Small Molecule Inhibitors of DENV Entry

In certain embodiments, the invention relates to the identification of an unexpected, previously unknown viral target for GNF-2, known to be a small molecule inhibitor of intracellular Abl kinases. GNF-2 reduces DENV infectivity as measured in yield reduction assays either when present on the cells after initial infection or when the compound is pre-incubated with virus inoculum. This latter inhibition appears to be Abl-independent and target the dengue virion itself. Using GNF-2 as a scaffold, we were able to identify several small molecule inhibitors of DENV entry that were inactive against Abl kinases.

GNF-2's anti-DENV activity during entry is not as potent as several other published DENV entry inhibitors, but it is unique among these entry inhibitors due to the fact that it also inhibits DENV at a later stage of the viral life cycle, most likely via its inhibition of cellular Abl kinases. GNF-2's inhibition of DENV via two separate targets via two independent mechanisms of action leads to the possible concept of dual-action viral inhibitors. The concept of using multi-targeted compounds to achieve a maximal therapeutic index is gaining traction in other areas of biomedicine, notably oncology. This concept has been tentatively explored previously in other viruses. One HIV study identified a peptide that inhibits glycoprotein gp120 interactions with both of its cell protein ligands, while another study discovered a small molecule that inhibits two separate steps of the HIV integration process. For rhinovirus, an inhibitor was identified that prevented activity of two separate viral proteases. However, our results for GNF-2 reveal a molecule that inhibits not at two points during one step of the viral life cycle, but rather acts at two separate points in the viral life cycle and is likely doing so via two separate targets. This concept is not without precedent; a dendrimer was identified that inhibited both herpes simplex virus (HSV) and late stages of viral replication, although potential target(s) of the molecule were not explored. We propose that it may be possible to use rational design to identify molecules that can inhibit viruses via two separate targets at separate points in the viral life cycle. The targets could be viral, cellular, or both, as we believe is the case for GNF-2. The challenging part of this approach would be to balance optimization of inhibitor activity between the two targets. While such dual-action inhibitors would be attractive due to their potentially higher barriers to viral resistance, this proposition remains to be experimentally explored.

The order of addition and the MOI titration experiments, as well as the fact that 2-12-2 inhibits DENV fusion in vitro, a process mediated by E, strongly suggest that small molecule 2-12-2, identified in the SAR study, targets the virion or dengue E protein. It is possible, although unlikely, that GNF-2 and 2-12-2 interact non-specifically with the lipid envelope of the virus. In addition, the location of binding on the E protein remains unknown for GNF-2 and 2-12-2; it is possible that binding sites for these two molecules may differ. We hypothesize that GNF-2 also inhibits DENV infectivity at the step of viral fusion, but due to the parental compound's lower potency, we were not able to test it in our in vitro assays. Thus, it is possible that GNF-2 may block a different step of DENV entry. Regardless of the step GNF-2 inhibits, however, it proved valuable as a scaffold in our SAR study, and led to the identification of several molecules that were up to five times more potent in cellular assays.

One potential binding location on the E protein for GNF-2 is the "hinge region" located between domains I and II. This site has previously been shown to be a ligand binding site, as crystallization of recombinant E revealed a single molecule of beta-octoglucoside (BOG) in the pocket formed by domains I and II. Several other small molecule inhibitors of DENV entry have also been hypothesized to bind in this area. However, binding in this region was originally predicted to inhibit the extension of domain II of E away from the viral membrane and hence block the insertion of the fusion loops into a target membrane. Interestingly, the M196V resistance mutation, described herein, is located at the base of this pocket. This mutation reduces the affinity of soluble prefusion E dimer for a biotinylated version of GNF2 by 30-fold ($K_D$ wildtype around 1 µM, $K_D$ mutant around 30 µM). This mutation also decreases the sensitivity of dengue serotype 2 reporter viruses. These observations are consistent with the idea that GNF2, 2-12-2, etc., may bind in the BOG pocket.

A previous study identified two other regions of the E protein that were predicted to be potential small molecule binding locations that prevent conformational changes of E that occur after insertion of the fusion (Yennamalli et al., 2009), so it is possible that our compounds could bind in either of these additional locations.

The work presented here reveals that GNF-2, a previously identified Abl kinase inhibitor, has an Abl-independent inhibitory effect on DENV entry, and this effect is likely mediated through interactions with the dengue virion itself. Using GNF-2 as a scaffold, we were able to identify several disubstituted pyrimidines that lower DENV yield by one log at single-digit micromolar concentrations when pre-incubated with virus inoculum. Further exploration of GNF-2 as a scaffold may identify even more potent DENV entry inhibitors. In addition, this study raises the possibility of rationally designing dual-target small molecule inhibitors of virus infection.

Definitions

In order for the invention to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The definition of each expression, e.g., alkyl, m, n, and the like, when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., a compound which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein below. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "lower" when appended to any of the groups listed below indicates that the group contains less than seven carbons (i.e. six carbons or less). For example "lower alkyl" refers to an alkyl group containing 1-6 carbons, and "lower alkenyl" refers to an alkenyl group containing 2-6 carbons.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond.

The term "aliphatic," as used herein, pertains to compounds and/or groups which are linear or branched, but not cyclic (also known as "acyclic" or "open-chain" groups).

The term "cyclic," as used herein, pertains to compounds and/or groups which have one ring, or two or more rings (e.g., spiro, fused, bridged).

The term "aromatic" refers to a planar or polycyclic structure characterized by a cyclically conjugated molecular moiety containing 4n+2 electrons, wherein n is the absolute value of an integer. Aromatic molecules containing fused, or joined, rings also are referred to as bicyclic aromatic rings. For example, bicyclic aromatic rings containing heteroatoms in a hydrocarbon ring structure are referred to as bicyclic heteroaryl rings.

The term "hydrocarbon" as used herein refers to an organic compound consisting entirely of hydrogen and carbon.

For purposes of this invention, the chemical elements are identified in accordance with the Periodic Table of the Elements, CAS version, Handbook of Chemistry and Physics, 67th Ed., 1986-87, inside cover.

The term "heteroatom" as used herein is art-recognized and refers to an atom of any element other than carbon or hydrogen. Illustrative heteroatoms include boron, nitrogen, oxygen, phosphorus, sulfur and selenium.

The term "alkyl" means an aliphatic or cyclic hydrocarbon radical containing from 1 to 12 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 2-methylcyclopentyl, and 1-cyclohexylethyl.

The term "substituted alkyl" means an aliphatic or cyclic hydrocarbon radical containing from 1 to 12 carbon atoms, substituted with 1, 2, 3, 4, or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, halo alkylcarbonyloxy, fluoroalkylcarbonyloxy, alkenylcarbonyloxy, alkynylcarbonyloxy, alkylsulfonyloxy, halo alkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, halo alkylsulfinyloxy, fluoroalkylsulfinyloxy, alkenylsulfinyloxy, alkynylsulfinyloxy, alkoxysulfinyloxy, halo alkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl and silyloxy.

The term "alkylene" is art-recognized, and as used herein pertains to a bidentate moiety obtained by removing two hydrogen atoms of an alkyl group, as defined above.

The term "alkenyl" as used herein means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl" as used herein means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "carbocyclyl" as used herein means monocyclic or multicyclic (e.g., bicyclic, tricyclic, etc.) hydrocarbons containing from 3 to 12 carbon atoms that is completely saturated or has one or more unsaturated bonds, and for the avoidance of doubt, the degree of unsaturation does not result in an aromatic ring system (e.g. phenyl). Examples of carbocyclyl groups include 1-cyclopropyl, 1-cyclobutyl, 2-cyclopentyl, 1-cyclopentenyl, 3-cyclohexyl, 1-cyclohexenyl and 2-cyclopentenylmethyl.

The term "heterocyclyl", as used herein include non-aromatic, ring systems, including, but not limited to, monocyclic, bicyclic (e.g. fused and spirocyclic) and tricyclic rings, which can be completely saturated or which can contain one or more units of unsaturation, for the avoidance of doubt, the degree of unsaturation does not result in an aromatic ring system, and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinyl, piperazinyl, piperidinyl, pyrrolidinyl, quinicludinyl, thiomorpholinyl, tetrahydropyranyl and tetrahydrofuranyl. The heterocyclyl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, halo alkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, halo alkylcarbonyloxy, fluoroalkylcarbonyloxy, alkenylcarbonyloxy, alkynylcarbonyloxy, alkylsulfonyloxy, halo alkylsulfonyloxy, fluoroalkylsulfonyloxy, alkenylsulfonyloxy, alkynylsulfonyloxy, halo alkoxysulfonyloxy, fluoroalkoxysulfonyloxy, alkenyloxysulfonyloxy, alkynyloxysulfonyloxy, alkylsulfinyloxy, halo alkylsulfinyloxy, fluoroalkylsulfinyloxy, alkenylsulfinyloxy, alkynylsulfinyloxy, alkoxysulfinyloxy, halo alkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heterocyclyl group through an alkylene moiety (e.g. methylene).

The term "N-heterocyclyl" as used herein is a subset of heterocyclyl, as defined herein, which have at least one nitrogen atom through which the N-heterocyclyl moiety is bound to the parent moiety. Representative examples include pyrrolidin-1-yl, piperidin-1-yl, piperazin-1-yl, hexahydropyrimidin-1-yl, morpholin-1-yl, 1,3-oxazinan-3-yl and 6-azaspiro[2.5]oct-6-yl. As with the heterocyclyl groups, the N-heterocyclyl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, halo alkylcarbonyloxy, fluoroalkylcarbonyloxy, alkenylcarbonyloxy, alkynylcarbonyloxy, alkylsulfonyloxy, halo alkylsulfonyloxy, fluoroalkylsulfonyloxy, alkenylsulfonyloxy, alkynylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, halo alkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the N-heterocyclyl group through an alkylene moiety (e.g. methylene).

The term "aryl," as used herein means a phenyl group, naphthyl or anthracenyl group. The aryl groups of the invention can be optionally substituted with 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, haloalkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, halo alkylcarbonyloxy, fluoroalkylcarbonyloxy, alkenylcarbonyloxy, alkynylcarbonyloxy, alkylsulfonyloxy, halo alkylsulfonyloxy, fluoroalkylsulfonyloxy, alkenylsulfonyloxy, alkynylsulfonyloxy, halo alkoxysulfonyloxy, fluoroalkoxysulfonyloxy, alkenyloxysulfonyloxy, alkynyloxysulfonyloxy, alkylsulfinyloxy, halo alkylsulfinyloxy, fluoroalkylsulfinyloxy, alkenylsulfinyloxy, alkynylsulfinyloxy, alkoxysulfinyloxy, halo alkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heterocyclyl group through an alkylene moiety (e.g. methylene).

The term "arylene," is art-recognized, and as used herein pertains to a bidentate moiety obtained by removing two hydrogen atoms of an aryl ring, as defined above.

The term "arylalkyl" or "aralkyl" as used herein means an aryl group, as defined herein, appended to the parent molecular moiety through an alkyl group, as defined herein. Representative examples of aralkyl include, but are not limited to, benzyl, 2-phenylethyl, 3-phenylpropyl, and 2-naphth-2-ylethyl.

The term "biaryl," as used herein means an aryl-substituted aryl, an aryl-substituted heteroaryl, a heteroaryl-substituted aryl or a heteroaryl-substituted heteroaryl, wherein aryl and heteroaryl are as defined herein. Representative examples include 4-(phenyl)phenyl and 4-(4-fluorophenyl)pyridinyl.

The term "heteroaryl" as used herein include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzotriazolyl, benzoxadiazolyl, furanyl, imidazolyl, imidazopyridinyl, indolyl, indolinyl, indazolyl, isoindolinyl, isoxazolyl, isothiazolyl, isoquinolinyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl, triazolyl or tropanyl. The heteroaryl groups of the invention are substituted with 0, 1, 2, 3, 4 or 5 substituents independently selected from the group consisting of alkyl, alkenyl, alkynyl, halo, haloalkyl, fluoroalkyl, hydroxy, alkoxy, alkenyloxy, alkynyloxy, carbocyclyloxy, heterocyclyloxy, haloalkoxy, fluoroalkyloxy, sulfhydryl, alkylthio, haloalkylthio, fluoroalkylthio, alkenylthio, alkynylthio, sulfonic acid, alkylsulfonyl, haloalkylsulfonyl, fluoroalkylsulfonyl, alkenylsulfonyl, alkynylsulfonyl, alkoxysulfonyl, halo alkoxysulfonyl, fluoroalkoxysulfonyl, alkenyloxysulfonyl, alkynyloxysulfonyl, aminosulfonyl, sulfinic acid, alkylsulfinyl, haloalkylsulfinyl, fluoroalkylsulfinyl, alkenylsulfinyl, alkynylsulfinyl, alkoxysulfinyl, haloalkoxysulfinyl, fluoroalkoxysulfinyl, alkenyloxysulfinyl, alkynyloxysulfiny, aminosulfinyl, formyl, alkylcarbonyl, haloalkylcarbonyl, fluoroalkylcarbonyl, alkenylcarbonyl, alkynylcarbonyl, carboxy, alkoxycarbonyl, haloalkoxycarbonyl, fluoroalkoxycarbonyl, alkenyloxycarbonyl, alkynyloxycarbonyl, alkylcarbonyloxy, halo alkylcarbonyloxy, fluoroalkylcarbonyloxy, alkenylcarbonyloxy, alkynylcarbonyloxy, alkylsulfonyloxy, halo alkylsulfonyloxy, fluoroalkylsulfonyloxy, alkenylsulfonyloxy, alkynylsulfonyloxy, haloalkoxysulfonyloxy, fluoroalkoxysulfonyloxy, alkenyloxysulfonyloxy, alkynyloxysulfonyloxy, alkylsulfinyloxy, halo alkylsulfinyloxy, fluoroalkylsulfinyloxy, alkenylsulfinyloxy, alkynylsulfinyloxy, alkoxysulfinyloxy, haloalkoxysulfinyloxy, fluoroalkoxysulfinyloxy, alkenyloxysulfinyloxy, alkynyloxysulfinyloxy, aminosulfinyloxy, amino, amido, aminosulfonyl, aminosulfinyl, cyano, nitro, azido, phosphinyl, phosphoryl, silyl, silyloxy, and any of said substituents bound to the heteroaryl group through an alkylene moiety (e.g. methylene).

The term "heteroarylene," is art-recognized, and as used herein pertains to a bidentate moiety obtained by removing two hydrogen atoms of a heteroaryl ring, as defined above.

The term "heteroarylalkyl" or "heteroaralkyl" as used herein means a heteroaryl, as defined herein, appended to the parent molecular moiety through an alkyl group, as defined herein. Representative examples of heteroarylalkyl include, but are not limited to, pyridin-3-ylmethyl and 2-(thien-2-yl) ethyl.

The term "halo" or "halogen" means —Cl, —Br, —I or —F.

The term "haloalkyl" means an alkyl group, as defined herein, wherein at least one hydrogen is replaced with a halogen, as defined herein. Representative examples of haloalkyl include, but are not limited to, chloromethyl, 2-fluoroethyl, trifluoromethyl, pentafluoroethyl, and 2-chloro-3-fluoropentyl.

The term "fluoroalkyl" means an alkyl group, as defined herein, wherein all the hydrogens are replaced with fluorines.

The term "hydroxy" as used herein means an —OH group.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The terms "alkenyloxy", "alkynyloxy", "carbocyclyloxy", and "heterocyclyloxy" are likewise defined.

The term "haloalkoxy" as used herein means an alkoxy group, as defined herein, wherein at least one hydrogen is replaced with a halogen, as defined herein. Representative examples of haloalkoxy include, but are not limited to, chloromethoxy, 2-fluoroethoxy, trifluoromethoxy, and pentafluoroethoxy. The term "fluoroalkyloxy" is likewise defined.

The term "aryloxy" as used herein means an aryl group, as defined herein, appended to the parent molecular moiety through an oxygen. The term "heteroaryloxy" as used herein means a heteroaryl group, as defined herein, appended to the parent molecular moiety through an oxygen. The terms "heteroaryloxy" is likewise defined.

The term "arylalkoxy" or "arylalkyloxy" as used herein means an arylalkyl group, as defined herein, appended to the parent molecular moiety through an oxygen. The term "heteroarylalkoxy" is likewise defined. Representative examples of aryloxy and heteroarylalkoxy include, but are not limited to, 2-chlorophenylmethoxy, 3-trifluoromethylphenylethoxy, and 2,3-dimethylpyridinylmethoxy.

The term "sulfhydryl" or "thio" as used herein means a —SH group.

The term "alkylthio" as used herein means an alkyl group, as defined herein, appended to the parent molecular moiety through a sulfur. Representative examples of alkylthio include, but are not limited, methylthio, ethylthio, tert-butylthio, and hexylthio. The terms "haloalkylthio", "fluoroalkylthio", "alkenylthio", "alkynylthio", "carbocyclylthio", and "heterocyclylthio" are likewise defined.

The term "arylthio" as used herein means an aryl group, as defined herein, appended to the parent molecular moiety through an sulfur. The term "heteroarylthio" is likewise defined.

The term "arylalkylthio" or "aralkylthio" as used herein means an arylalkyl group, as defined herein, appended to the parent molecular moiety through an sulfur. The term "heteroarylalkylthio" is likewise defined.

The term "sulfonyl" as used herein refers to —S(=O)$_2$— group.

The term "sulfonic acid" as used herein refers to —S(=O)$_2$OH.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl. The terms "haloalkylsulfonyl", "fluoroalkylsulfonyl", "alkenylsulfonyl", "alkynylsulfonyl", "carbocyclylsulfonyl", "heterocyclylsulfonyl", "arylsulfonyl", "aralkylsulfonyl", "heteroarylsulfonyl" and "heteroaralkylsulfonyl" are likewise defined.

The term "alkoxysulfonyl" as used herein means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl. The terms "haloalkoxysulfonyl", "fluoroalkoxysulfonyl", "alkenyloxysulfonyl", "alkynyloxysulfonyl", "carbocyclyloxysulfonyl", "heterocyclyloxysulfonyl", "aryloxysulfonyl", "aralkyloxysulfonyl", "heteroaryloxysulfonyl" and "heteroaralkyloxysulfonyl" are likewise defined.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "aminosulfonyl" as used herein means an amino group, as defined herein, appended to the parent molecular moiety through a sulfonyl group.

The term "sulfinyl" as used herein refers to —S(=O)— group. Sulfinyl groups are as defined above for sulfonyl groups. The term "sulfinic acid" as used herein refers to —S(=O)OH.

The term "oxy" refers to a —O— group.

The term "carbonyl" as used herein means a —C(=O)— group.

The term "thiocarbonyl" as used herein means a —C(=S)— group.

The term "formyl" as used herein means a —C(=O)H group.

The term "alkylcarbonyl" as used herein means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl. The terms "haloalkylcarbonyl", "fluoroalkylcarbonyl", "alkenylcarbonyl", "alkynylcarbonyl", "carbocyclylcarbonyl", "heterocyclylcarbonyl", "arylcarbonyl", "aralkylcarbonyl", "heteroarylcarbonyl", and "heteroaralkylcarbonyl" are likewise defined.

The term "carboxy" as used herein means a —CO$_2$H group.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl. The terms "haloalkoxycarbonyl", "fluoroalkoxycarbonyl", "alkenyloxycarbonyl", "alkynyloxycarbonyl", "carbocyclyloxycarbonyl", "heterocyclyloxycarbonyl", "aryloxycarbonyl", "aralkyloxycarbonyl", "heteroaryloxycarbonyl", and "heteroaralkyloxycarbonyl" are likewise defined.

The term "alkylcarbonyloxy" as used herein means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy. The terms "haloalkylcarbonyloxy", "fluoroalkylcarbonyloxy", "alkenylcarbonyloxy", "alkynylcarbonyloxy", "carbocyclylcarbonyloxy", "heterocyclylcarbonyloxy", "arylcarbonyloxy", "aralkylcarbonyloxy", "heteroarylcarbonyloxy", and "heteroaralkylcarbonyloxy" are likewise defined.

The term "alkylsulfonyloxy" as used herein means an alkylsulfonyl group, as defined herein, appended to the parent molecular moiety through an oxygen atom. The terms "haloalkylsulfonyloxy", "fluoroalkylsulfonyloxy", "alkenylsulfonyloxy", "alkynylsulfonyloxy", "carbocyclylsulfonyloxy", "heterocyclylsulfonyloxy", "arylsulfonyloxy", "aralkylsulfonyloxy", "heteroarylsulfonyloxy", "heteroaralkylsulfonyloxy", "haloalkoxysulfonyloxy", "fluoroalkoxysulfonyloxy", "alkenyloxysulfonyloxy", "alkynyloxysulfonyloxy", "carbocyclyloxysulfonyloxy", "heterocyclyloxysulfonyloxy", "aryloxysulfonyloxy", "aralkyloxysulfonyloxy", "heteroaryloxysulfonyloxy" and "heteroaralkyloxysulfonyloxy"

The term "amino" as used herein refers to —NH$_2$ and substituted derivatives thereof wherein one or both of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkylcarbonyl, haloalkylcarbonyl, fluoroalkylcarbonyl, alkenylcarbonyl, alkynylcarbonyl, carbocyclylcarbonyl, heterocyclylcarbonyl, arylcarbonyl, aralkylcarbonyl, heteroarylcarnbonyl, heteroaralkylcarbonyl and the sulfonyl and sulfinyl groups defined above; or when both hydrogens together are replaced with an alkylene group (to form a ring which contains the nitrogen). Representative examples include, but are not limited to methylamino, acetylamino, and dimethylamino.

The term "amido" as used herein means an amino group, as defined herein, appended to the parent molecular moiety through a carbonyl.

The term "cyano" as used herein means a —C≡N group.

The term "nitro" as used herein means a —NO$_2$ group.

The term "azido" as used herein means a —N$_3$ group.

The term "phosphinyl" as used herein includes —PH$_3$ and substituted derivatives thereof wherein one, two or three of the hydrogens are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "phosphoryl" as used herein refers to —P(=O)OH$_2$ and substituted derivatives thereof wherein one or both of the hydroxyls are independently replaced with substituents selected from the group consisting of alkyl, haloalkyl, fluoroalkyl, alkenyl, alkynyl, carbocyclyl, heterocyclyl, aryl, aralkyl, heteroaryl, heteroaralkyl, alkoxy, haloalkoxy, fluoroalkyloxy, alkenyloxy, alkynyloxy, carbocyclyloxy, heterocyclyloxy, aryloxy, aralkyloxy, heteroaryloxy, heteroaralkyloxy, and amino.

The term "silyl" as used herein includes H$_3$Si— and substituted derivatives thereof wherein one, two or three of the hydrogens are independently replaced with substituents selected from alkyl, haloalkyl, fluoroalkyl, alkenyl, alkynyl, carbocyclyl, heterocyclyl, aryl, aralkyl, heteroaryl, and heteroaralkyl. Representative examples include trimethylsilyl (TMS), tert-butyldiphenylsilyl (TBDPS), tert-butyldimethylsilyl (TB S/TBDMS), triisopropylsilyl (TIPS), and [2-(trimethylsilyl)ethoxy]methyl (SEM).

The term "silyloxy" as used herein means a silyl group, as defined herein, is appended to the parent molecule through an oxygen atom.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

As used herein, the term "administering" means providing a pharmaceutical agent or composition to a subject, and includes, but is not limited to, administering by a medical professional and self-administering.

As used herein, the phrase "pharmaceutically acceptable" refers to those agents, compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the phrase "pharmaceutically-acceptable carrier" means a pharmaceutically-acceptable material, composition or vehicle, such as a liquid or solid filler, diluent, excipient, or solvent encapsulating material, involved in carrying or transporting an agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As used herein, the phrase "pharmaceutically-acceptable salts" refers to the relatively non-toxic, inorganic and organic salts of compounds.

The term "viral infection" as used herein refers to infection by a viral pathogen wherein there is clinical evidence of the infection based on symptoms or based on the demonstration of the presence of the viral pathogen in a biological sample from the individual. As used herein an "individual" refers to an animal, preferably a mammal, including both non-human mammals and humans, and more preferably, refers to a human.

"Treatment of a viral infection" as used herein encompasses alleviating, reducing the frequency of, or eliminating one or more symptoms of the infection and/or a reducing the viral load.

As used herein, the term "subject" means a human or non-human animal selected for treatment or therapy.

As used herein, the phrase "subject suspected of having" means a subject exhibiting one or more clinical indicators of a disease or condition.

As used herein, the phrase "subject in need thereof" means a subject identified as in need of a therapy or treatment of the invention.

As used herein, the phrase "therapeutic effect" refers to a local or systemic effect in animals, particularly mammals, and more particularly humans, caused by an agent. The phrases "therapeutically-effective amount" and "effective amount" mean the amount of an agent that produces some therapeutically useful effect on the symptoms of the viral infection and/or a reduction in viral load. A therapeutically effective amount includes an amount of an agent that produces some desired local or systemic effect at a reasonable benefit/risk ratio applicable to any treatment. For example, certain agents used in the methods of the invention may be administered in a sufficient amount to produce a reasonable benefit/risk ratio applicable to such treatment.

As used herein, the term "treating" a disease in a subject or "treating" a subject having or suspected of having a disease refers to subjecting the subject to a pharmaceutical treatment, e.g., the administration of an agent, such that at least one symptom of the disease is decreased or prevented from worsening.

As used herein, the phrase "inhibiting replication" means to reduce replication of a virus in a host cell by about 20%, about 30%, about 40%, about 50%, about 60%, about 70%, about 80%, about 90%, or about 95%, in comparison to an untreated cell. In certain embodiments, "inhibiting replication" means to reduce replication of a virus in a host cell by at least about 50%, in comparison to an untreated cell.

Compounds of the Invention

In certain embodiments, the invention relates to a compound, or a pharmaceutically acceptable salt, solvate, hydrate, prodrug, chemically-protected form, enantiomer or stereoisomer thereof, wherein the compound is represented by formula I

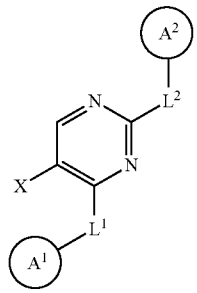

Formula I wherein, independently for each occurrence,

is optionally substituted aryl, optionally substituted heteroaryl, optionally substituted aralkyl, or optionally substituted heteroaralkyl;

is optionally substituted aryl, optionally substituted heteroaryl, optionally substituted aralkyl, or optionally substituted heteroaralkyl;

$L^1$ is a bond, —NR—, —O—, $CR_2$—, —S—, —$(CR_2)_2$—, —C(O)—NR—, —NR—C(O)—, —C(O)O—, —O—C(O)—, —$OCR_2$—, —$CR_2O$—, —NR—$CR_2$—, or —$CR_2$—NR—;

$L^2$ is a bond, —NR—, —O—, $CR_2$—, —S—, —$(CR_2)_2$—, —C(O)—NR—, —NR—C(O)—, —C(O)O—, —O—C(O)—, —$OCR_2$—, —$CR_2O$—, —NR—$CR_2$—, or —$CR_2$—NR—;

X is H or halo; and

R is H, alkyl, aryl, or aralkyl.

In certain embodiments, the invention relates to a compound, or a pharmaceutically acceptable salt, solvate, hydrate, prodrug, chemically-protected form, enantiomer or stereoisomer thereof, wherein the compound is represented by formula II

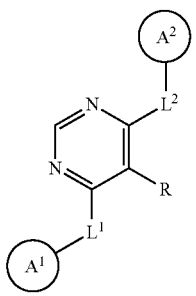

Formula II wherein, independently for each occurrence,

is optionally substituted aryl, optionally substituted heteroaryl, optionally substituted aralkyl, or optionally substituted heteroaralkyl;

is optionally substituted aryl, optionally substituted heteroaryl, optionally substituted aralkyl, or optionally substituted heteroaralkyl;

$L^1$ is a bond, —NR—, —O—, $CR_2$—, —S—, —$(CR_2)_2$—, —C(O)—NR—, —NR—C(O)—, —C(O)O—, —O—C(O)—, —$OCR_2$—, —$CR_2O$—, —NR—$CR_2$—, or —$CR_2$—NR—;

$L^2$ is a bond, —NR—, —O—, $CR_2$—, —S—, —$(CR_2)_2$—, —C(O)—NR—, —NR—C(O)—, —C(O)O—, —O—C(O)—, —$OCR_2$—, —$CR_2O$—, —NR—$CR_2$—, or —$CR_2$—NR—; and R is H, alkyl, aryl, or aralkyl, provided the compound is not

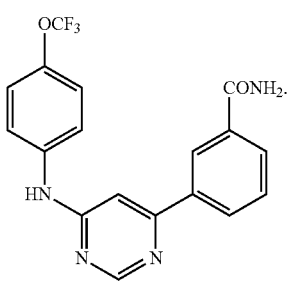

In certain embodiments, the invention relates to any one of the aforementioned compounds, wherein

is substituted or unsubstituted aryl. In certain embodiments, the invention relates to any one of the aforementioned compounds, wherein

is substituted or unsubstituted phenyl. In certain embodiments, the invention relates to any one of the aforementioned compounds, wherein

is substituted or unsubstituted naphthyl.

In certain embodiments, the invention relates to any one of the aforementioned compounds, wherein

is substituted or unsubstituted aralkyl. In certain embodiments, the invention relates to any one of the aforementioned compounds, wherein

is substituted or unsubstituted benzyl.

In certain embodiments, the invention relates to any one of the aforementioned compounds, wherein

is substituted or unsubstituted aryl. In certain embodiments, the invention relates to any one of the aforementioned compounds, wherein

is substituted or unsubstituted phenyl.

In certain embodiments, the invention relates to any one of the aforementioned compounds, wherein

is substituted or unsubstituted heteroaryl. In certain embodiments, the invention relates to any one of the aforementioned compounds, wherein

is substituted or unsubstituted pyrazolyl or imidazolyl.

In certain embodiments, the invention relates to any one of the aforementioned compounds, wherein

is substituted with one or more substituents selected from the group consisting of alkoxy, alkyl, —C(O)NR$_2$, —C(O)OR, fluoroalkyl, fluoroalkyloxy, aminoalkyl, hydroxyalkyl, halo, cyano, nitro, aryl, heteroaryl, aralkyl, heteroaralkyl, —(OCH$_2$CH$_2$)$_n$—NH$_2$ (wherein n is 1, 2, 3, 4, 5, 6, 7, 8, 9, or 10), heterocyclylalkyl, —SO$_2$NR$_2$, aminoalkyl, aryloxy, and heteroaryloxy. In certain embodiments, the invention relates to any one of the aforementioned compounds, wherein

is substituted with one or more substituents selected from the group consisting of alkoxy, fluoroalkyl, fluoroalkyloxy, aminoalkyl, hydroxyalkyl, halo, cyano, and nitro. In certain embodiments, the invention relates to any one of the aforementioned compounds, wherein

is substituted with one or more substituents selected from the group consisting of —OCF$_3$ and —CF$_3$. In certain embodiments, the invention relates to any one of the aforementioned compounds, wherein

is substituted with one or more substituents selected from the group consisting of heteroaralkyl, heterocyclylalkyl, —SO$_2$NR$_2$, and aminoalkyl. In certain embodiments, the invention relates to any one of the aforementioned compounds, wherein

is substituted with one or more substituents selected from the group consisting of heteroaralkyl, heterocyclylalkyl, —SO$_2$NR$_2$, and aminoalkyl.

In certain embodiments, the invention relates to any one of the aforementioned compounds, wherein

is substituted with a fluorescent group. In certain embodiments, the invention relates to any one of the aforementioned compounds, wherein

is substituted with fluorescein isothiocyanate. In certain embodiments, the invention relates to any one of the aforementioned compounds, wherein

is substituted with boron-dipyrromethene.

In certain embodiments, the invention relates to any one of the aforementioned compounds, wherein

is substituted with a targeting moiety. In certain embodiments, the invention relates to any one of the aforementioned compounds, wherein

is substituted with biotin.

In certain embodiments, the invention relates to any one of the aforementioned compounds, wherein

is substituted with a solubilizing group. In certain embodiments, the invention relates to any one of the aforementioned compounds, wherein

is substituted with heterocycloalkyl. In certain embodiments, the invention relates to any one of the aforementioned compounds, wherein

is substituted with alkyl-substituted heterocycloalkyl. In certain embodiments, the invention relates to any one of the aforementioned compounds, wherein

is substituted with heterocycloalkyl-substituted alkyl. In certain embodiments, the invention relates to any one of the aforementioned compounds, wherein

is substituted with alkyl-substituted heterocycloalkyl alkyl. In certain embodiments, the invention relates to any one of the aforementioned compounds, wherein

is substituted with alkoxy. In certain embodiments, the invention relates to any one of the aforementioned compounds, wherein

is substituted with heterocycloalkyl-substituted alkoxy. In certain embodiments, the invention relates to any one of the aforementioned compounds, wherein

is substituted with haloalkyl. In certain embodiments, the invention relates to any one of the aforementioned compounds, wherein

is substituted with fluoroalkyl. In certain embodiments, the invention relates to any one of the aforementioned compounds, wherein

is substituted with trifluoromethyl.

In certain embodiments, the fluorescent group, the targeting moiety, or the solubilizing moiety is covalently bonded to a linker, which, in turn, is covalently bonded to

.

In certain embodiments, the linker is an oligooxyalkylene chain. In certain embodiments, the linker is an oligooxyethylene chain. In certain embodiments, covalent bond linking the linker to the compound or to the fluorescent group, the targeting moiety, or the solubilizing group is an amide bond.

In certain embodiments, the invention relates to any one of the aforementioned compounds, wherein $L^1$ is —NR— or —O—. In certain embodiments, the invention relates to any one of the aforementioned compounds, wherein $L^1$ is —NR—. In certain embodiments, the invention relates to any one of the aforementioned compounds, wherein $L^1$ is —NH—.

In certain embodiments, the invention relates to any one of the aforementioned compounds, wherein $L^2$ is —NR— or —O—. In certain embodiments, the invention relates to any one of the aforementioned compounds, wherein $L^2$ is —NR—. In certain embodiments, the invention relates to any one of the aforementioned compounds, wherein $L^2$ is —NH—.

In certain embodiments, the invention relates to any one of the aforementioned compounds, wherein $L^2$ is a bond.

In certain embodiments, the invention relates to any one of the aforementioned compounds, wherein the compound is selected from the group consisting of

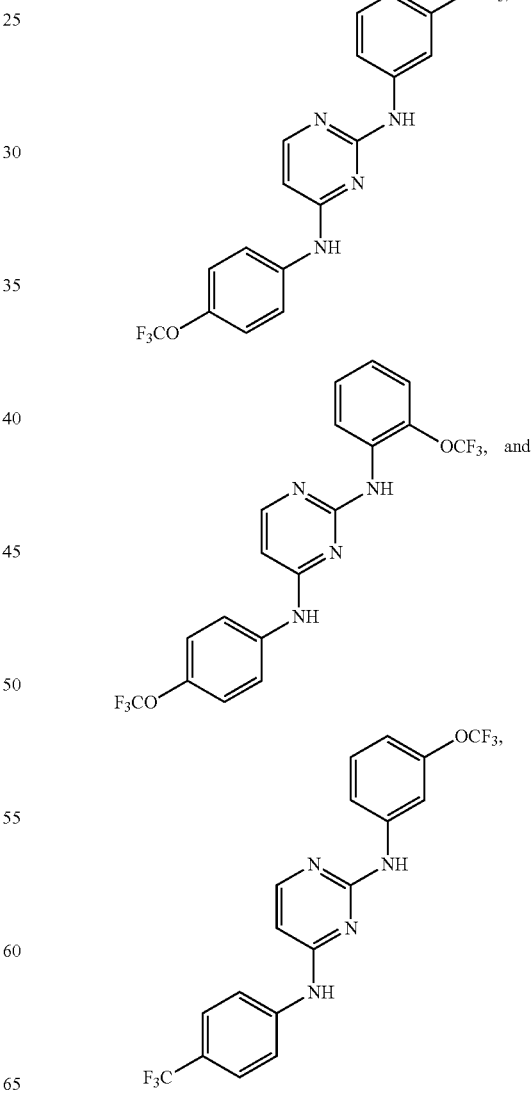

-continued

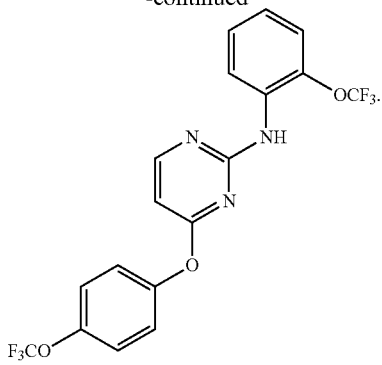

In certain embodiments, the invention relates to any one of the aforementioned compounds, wherein the compound is a compound defined in FIG. 17, FIG. 18, FIG. 19, FIG. 20, FIG. 26, FIG. 27, FIG. 28, or FIG. 29.

In certain embodiments, the invention relates to any one of the aforementioned compounds, wherein the compound is selected from the group consisting of

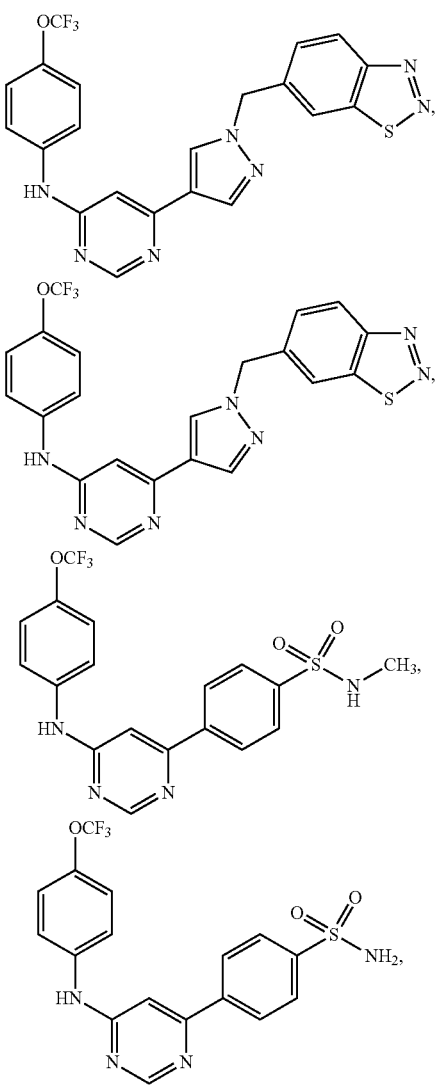

-continued

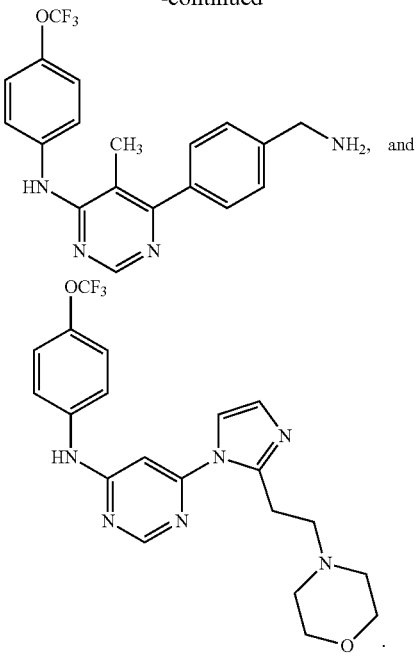

Therapeutic Methods of the Invention

In certain embodiments, the invention relates to a method of inhibiting entry of a virus into a host cell comprising contacting the host cell with an effective amount of any one of the aforementioned compounds or

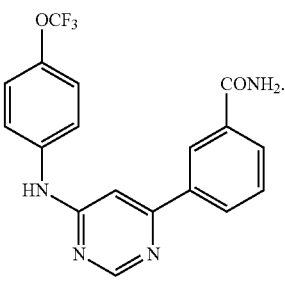 [SMILES: NC(=O)c1cccc(-c2cc(Nc3ccc(OC(F)(F)F)cc3)ncn2)c1]

In certain embodiments, the invention relates to a method of inhibiting replication of a virus in a host cell comprising contacting the host cell with an effective amount of any one of the aforementioned compounds or

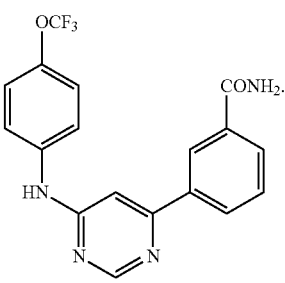 [SMILES: NC(=O)c1cccc(-c2cc(Nc3ccc(OC(F)(F)F)cc3)ncn2)c1]

In certain embodiments, the invention relates to a method of inhibiting fusion of a virus to the cell membrane of a host cell comprising contacting the host cell with an effective amount of any one of the aforementioned compounds or

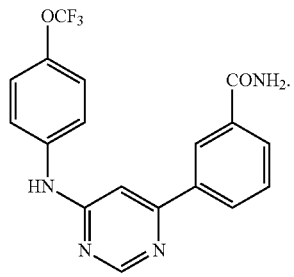 [SMILES: NC(=O)c1cccc(-c2cc(Nc3ccc(OC(F)(F)F)cc3)ncn2)c1]

In certain embodiments, the invention relates to any of the aforementioned methods, wherein the host cell is contacted with the compound before exposure to the virus.

In certain embodiments, the invention relates to any of the aforementioned methods, wherein the host cell is contacted with the compound after exposure to the virus.

In certain embodiments, the invention relates to any one of the aforementioned methods, wherein the virus is of family Flaviviridae.

In certain embodiments, the invention relates to any one of the aforementioned methods, wherein the virus is of genus *Flavivirus, Pestivirus,* or *Hepacivirus*. In certain embodiments, the invention relates to any one of the aforementioned methods, wherein the virus is of genus *Flavivirus*.

In certain embodiments, the invention relates to any one of the aforementioned methods, wherein the virus is dengue virus (DENV).

In certain embodiments, the invention relates to a method of treating or preventing a viral infection in a subject comprising administering to the subject, (e.g., a subject in need thereof), an effective amount of any one of the aforementioned compounds.

In certain embodiments, the invention relates to any of the aforementioned methods, wherein the compound is administered to the subject before exposure to a virus; and the virus causes the viral infection.

In certain embodiments, the invention relates to any of the aforementioned methods, wherein the compound is administered to the subject after exposure to a virus; and the virus causes the viral infection.

In certain embodiments, the invention relates to any one of the aforementioned methods, wherein the viral infection is a result of a virus of family Flaviviridae.

In certain embodiments, the invention relates to any one of the aforementioned methods, wherein the viral infection is a result of a virus of genus *Flavivirus, Pestivirus,* or *Hepacivirus*. In certain embodiments, the invention relates to any one of the aforementioned methods, wherein the viral infection is a result of a virus of genus *Flavivirus*. In certain embodiments, the invention relates to any one of the aforementioned methods, wherein the viral infection is a result of dengue virus (DENV).

In certain embodiments, the invention relates to any one of the aforementioned methods, wherein the viral infection is selected from the group consisting of: Dengue fever, Japanese encephalitis, Kyasanur Forest disease, Murray Valley encephalitis, St. Louis encephalitis, Tick-borne encephalitis, West Nile encephalitis, Yellow fever, and Hepatitis C.

The methods of the invention are useful for treating a subject in need thereof. A subject in need thereof is a subject having or at risk of having an enveloped virus infection. In its broadest sense, the terms "treatment" or "to treat" refer to both therapeutic and prophylactic treatments. If the subject in need of treatment is experiencing a condition (i.e., has or is having a particular condition), then "treating the condition" refers to ameliorating, reducing or eliminating one or more symptoms arising from the condition. If the subject in need of treatment is one who is at risk of having a condition, then treating the subject refers to reducing the risk of the subject having the condition or, in other words, decreasing the likelihood that the subject will develop an infectious disease to the virus, as well as to a treatment after the subject has been infected in order to fight the infectious disease, e.g., reduce or eliminate it altogether or prevent it from becoming worse.

Thus the invention encompasses the use of the compounds described herein alone or in combination with other therapeutics for the treatment of a subject having or at risk of having a viral infection, e.g., an enveloped viral infection. A "subject having an enveloped viral infection" is a subject that has had contact with a virus. Thus the virus has invaded the body of the subject. The word "invade" as used herein refers to contact by the virus with an external surface of the subject, e.g., skin or mucosal membranes and/or refers to the penetration of the external surface of the subject by the virus. A subject at risk of having an enveloped virus infection is one that has been exposed to or may become exposed to an enveloped virus or a geographical area in which an enveloped viral infection has been reported. Further risks include close contact with a human or non-human primate or their tissues infected with the virus. Such persons include laboratory or quarantine facility workers who handle non-human primates that have been associated with the disease. In addition, hospital staff and family members who care for patients with the disease are at risk if they do not use proper barrier nursing techniques.

As used herein, a subject includes humans and non-human animals such as non-human primates, dogs, cats, sheep, goats, cows, pigs, horses and rodents.

In certain embodiments, the methods of the invention are useful for treating infection with enveloped viruses. Viruses are small infectious agents which contain a nucleic acid core and a protein coat, but are not independently living organisms. A virus cannot multiply in the absence of a living cell within which it can replicate. Viruses enter specific living cells either by transfer across a membrane or direct injection and multiply, causing disease. The multiplied virus can then be released and infect additional cells. Some viruses are DNA-containing viruses and others are RNA-containing viruses. The genomic size, composition and organization of viruses show tremendous diversity.

As used herein, an "enveloped" virus is an animal virus which possesses a membrane or 'envelope', which is a lipid bilayer containing viral proteins. The envelope proteins of a virus play a pivotal role in its lifecycle. They participate in the assembly of the infectious particle and also play a crucial role in virus entry by binding to a receptor present on the host cell and inducing fusion between the viral envelope and a membrane of the host cell. Enveloped viruses can be either spherical or filamentous (rod-shaped) and include but are not limited to filoviruses, such as Ebola virus or Marburg virus, Lassa virus, Arboroviruses such as Togaviruses, flaviviruses (such as hepatitis-C virus), bunyaviruses, and Arenaviruses, Orthomyxoviridae, Paramyxoviridae, poxvirus, herpesvirus, hepadnavirus, Rhabdovirus, Bornavirus, and Arterivirus.

Flaviviridae is a member of the family of (+)-sense RNA enveloped viruses. Flaviviridae includes Flavivirus, Pestivirus, and Hepacivirus. The Flavivirus genus includes yellow fever virus, dengue fever virus, West Nile virus, and Japanese encephalitis (JE) virus. Major diseases caused by viruses in the Flaviviridae family include: Dengue fever, Japanese encephalitis, Kyasanur Forest disease, Murray Valley encephalitis, St. Louis encephalitis, Tick-borne encephalitis, West Nile encephalitis, Yellow fever, and Hepatitis C. The Pestivirus genus includes the three serotypes of bovine viral diarrhea, but no known human pathogens. Genus Hepacivirus consists of hepatitis C virus and hepatitis C-like viruses.

A yellow fever virus infection is characterized by an incubation period of 3 to 6 days, during which 5% to 50% of infected people develop disease. Yellow fever begins with a nonspecific 1- to 3-day febrile illness, followed by a brief remission, and then by a life-threatening toxic syndrome accompanied by epistaxis, other hemorrhagic phenomena, jaundice, and disseminated intravascular coagulation. Mortality rates for yellow fever are approximately 20%.

There are four serotypes of dengue fever virus, all transmitted by mosquitoes. Dengue fever virus infection may be asymptomatic or may result in dengue fever. This is generally a self-limiting febrile illness which occurs after a 4-8 day incubation period. It has symptoms such as fever, aches and arthralgia (pain in the joints) which can progress to arthritis (inflammation of the joints), myositis (inflammation of muscle tissue) and a discrete macular or maculopapular rash. In this situation clinical differentiation from other viral illnesses may not be possible, recovery is rapid, and need for supportive treatment is minimal. Dengue haemorrhagic fever (DHF) is a potentially deadly complication. Dengue hemorrhagic fever commences with high fever and many of the symptoms of dengue fever, but with extreme lethargy and drowsiness. The patient has increased vascular permeability and abnormal homeostasis that can lead to hypovolemia and hypotension, and in severe cases, result in hypovolemic shock often complicated by severe internal bleeding.

The Japanese encephalitis antigenic complex includes Alfuy, Japanese encephalitis, Kokobera, Koutango, Kunjin, Murray Valley encephalitis, St. Louis encephalitis, Stratford, Usutu, and West Nile viruses. These viruses are transmissible by mosquitoes and many of them can cause febrile, sometimes fatal, illnesses in humans. West Nile virus is the most widespread of the flaviviruses, with geographic distribution including Africa and Eurasia. West Nile virus RNA has been detected in overwintering mosquitoes in New York City & the geographic range of the virus is increasing in the USA.

The genus *Pestivirus* has been divided into bovine viral diarrhea virus (BVDV), classical swine fever virus (CSFV), and border disease virus (BDV). Infection with BVDV results in a variety of diseases ranging from subclinical to highly fatal. Many BVDV viruses cause only clinically mild disease in nonpregnant adult cattle. Prenatal infection can cause congenital malformations and/or fetal death.

The *Hepacivirus* genus includes the hepatitis C virus (HCV). The majority of cases of HCV infection give rise to an acute illness, where up to 85% of infections may develop into chronic hepatitis. Almost all patients develop a vigorous antibody and cell-mediated immune response which fails to clear the infection but may contribute towards liver damage.

In some embodiments, the desired dose of the active agent will depend on absorption, inactivation, and excretion rates of the drug as well as the delivery rate of the compound. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

The dosage of the active agent may be determined by reference to the plasma concentrations of the agent. For example, the maximum plasma concentration (Cmax) and the area under the plasma concentration-time curve from time 0 to infinity (AUC (0-4)) may be used. Dosages for the invention include those that produce the above values for Cmax and AUC (0-4) and other dosages resulting in larger or smaller values for those parameters.

Actual dosage levels of the active agents may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular agent employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could prescribe and/or administer doses of the agents of the invention employed in the pharmaceutical composition at levels lower than that required in order to achieve the desired therapeutic effect and gradually increase the dosage until the desired effect is achieved.

In general, a suitable daily dose of an agent of the invention will be that amount of the agent (e.g., the compound) which is the lowest dose effective to produce a therapeutic effect. Such an effective dose will generally depend upon the factors described above.

If desired, the effective daily dose of the agent may be administered as two, three, four, five, six or more sub-doses administered separately at appropriate intervals throughout the day, optionally, in unit dosage forms.

The precise time of administration and amount of any particular agent that will yield the most effective treatment in a given patient will depend upon the activity, pharmacokinetics, and bioavailability of a particular agent, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the subject may be monitored by measuring one or more of the relevant indices at predetermined times during a 24-hour period. All aspects of the treatment, including supplements, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments, for example, to the amount(s) of agent administered and to the time of administration may be made based on these reevaluations.

Treatment may be initiated with smaller dosages which are less than the optimum dose of the compound. Thereafter, the dosage may be increased by small increments until the optimum therapeutic effect is attained. In addition, the combined use of an antiviral agent of the invention and a second agent, e.g. another agent useful for the treatment or prevention of viral infections, may reduce the required dosage for any individual agent because the onset and duration of effect of the different compounds and/or agents may be complimentary.

Many of the compounds used in the methods of the invention may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a recipient. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Acids commonly employed to form pharmaceutically acceptable salts include inorganic acids such as hydrogen bisulfide, hydrochloric, hydrobromic, hydroiodic, sulfuric and phosphoric acid, as well as organic acids such as para-toluenesulfonic, salicylic, tartaric, bitartaric, ascorbic, maleic, besylic, fumaric, gluconic, glucuronic, formic, glutamic, methanesulfonic, ethanesulfonic, benzenesulfonic, lactic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, .beta.-hydroxybutyrate, glycolate, maleate, tartrate, methanesulfonate, propanesulfonate, naphthalene-1-sulfonate, naphthalene-2-sulfonate, mandelate and the like salts. Pharmaceutically acceptable acid addition salts include those formed with mineral acids such as hydrochloric acid and hydrobromic acid, and those formed with organic acids such as maleic acid.

Suitable bases for forming pharmaceutically acceptable salts with acidic functional groups include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N-di-lower alkyl-N-(hydroxy lower alkyl)-amines, such as N,N-dimethyl-N-(2-hydroxyethyl)amine, or tri-(2-hydroxyethyl) amine; N-methyl-D-glucamine; and amino acids such as arginine, lysine, and the like.

Certain compounds used in methods of the invention and their salts may exist in more than one crystal form and the invention includes each crystal form and mixtures thereof.

Certain compounds used in methods of the invention and their salts may also exist in the form of solvates, for example hydrates, and the invention includes each solvate and mixtures thereof.

Certain compounds used in methods of the invention may contain one or more chiral centers, and exist in different optically active forms. When compounds of the invention contain one chiral center, the compounds exist in two enantiomeric forms and the invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step may be used to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound used in the methods of the invention contains more than one chiral center, it may exist in diastereoisomeric forms. The diastereoisomeric compounds may be separated by methods known to those skilled in the art, for example chromatography or crystallization and the individual enantiomers may be separated as described above. The invention includes each diastereoisomer of compounds of the invention and mixtures thereof.

Certain compounds used in methods of the invention may exist in different tautomeric forms or as different geometric isomers, and the invention includes each tautomer and/or geometric isomer of compounds of the invention and mixtures thereof.

Certain compounds used in methods of the invention may exist in different stable conformational forms which may be separable. Torsional asymmetry due to restricted rotation about an asymmetric single bond, for example because of steric hindrance or ring strain, may permit separation of different conformers. The invention includes each conformational isomer of compounds of the invention and mixtures thereof.

Certain compounds used in methods of the invention may exist in zwitterionic form and the invention includes each zwitterionic form of compounds of the invention and mixtures thereof.

The invention also includes methods of using pro-drugs. As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The prodrug may also have improved solubility in pharmacological compositions over the parent drug. An example, without limitation, of a pro-drug would be a compound of the invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial. Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents (e.g., —C(O)$_2$H or a moiety that contains a carboxylic acid) wherein the free hydrogen is replaced by ($C_1$-$C_4$)alkyl, ($C_2$-$C_{12}$)alkanoyloxymethyl, ($C_4$-$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)-alkylcarbamoyl-($C_1$-$C_2$)alkyl and piperidino-, pyrrolidino- or morpholino($C_2$-$C_3$)alkyl.

Other exemplary pro-drugs release an alcohol or amine of a compound of the invention wherein the free hydrogen of a hydroxyl or amine substituent is replaced by ($C_1$-$C_6$) alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyl-oxymethyl, N—($C_1$-$C_6$)alkoxycarbonylaminomethyl, succinoyl, ($C_1$-$C_6$)alkanoyl, α-amino($C_1$-$C_4$)alkanoyl, arylactyl and α-aminoacyl, or α-aminoacyl-α-aminoacyl wherein said α-aminoacyl moieties are independently any of the naturally occurring L-amino acids found in proteins, —P(O)(OH)$_2$, —P(O)(O($C_1$-$C_6$)alkyl)$_2$ or glycosyl (the radical resulting from detachment of the hydroxyl of the hemiacetal of a carbohydrate).

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991). Protected forms of the inventive compounds are included within the scope of this invention.

The term "chemically protected form," as used herein, pertains to a compound in which one or more reactive functional groups are protected from undesirable chemical reactions, that is, are in the form of a protected or protecting group (also known as a masked or masking group). It may be convenient or desirable to prepare, purify, and/or handle the active compound in a chemically protected form.

By protecting a reactive functional group, reactions involving other unprotected reactive functional groups can be performed, without affecting the protected group; the protecting group may be removed, usually in a subsequent step, without substantially affecting the remainder of the molecule. See, for example, Protective Groups in Organic Synthesis (T. Green and P. Wuts, Wiley, 1991), and Protective Groups in Organic Synthesis (T. Green and P. Wuts; 3rd Edition; John Wiley and Sons, 1999).

For example, a hydroxy group may be protected as an ether (—OR) or an ester (—OC(=O)R), for example, as: a t-butyl ether; a benzyl, benzhydryl(diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal or ketal, respectively, in which the carbonyl group (C(=O)) is converted to a diether (C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRC(=O)R) or a urethane (—NRC(=O)OR), for example, as: a methyl amide (—NHC(=O)CH$_3$); a benzyloxy amide (—NHC(=O) OCH$_2$C$_6$H$_5$NHCbz); as a t-butoxy amide (—NHC(=O)OC (CH$_3$)$_3$, —NHBoc); a 2-biphenyl-2-propoxy amide (—NHC (=O)OC(CH$_3$)$_2$C$_6$H$_4$C$_6$H$_5$NHBoc), as a 9-fluorenylmethoxy amide (—NHFmoc), as a 6-nitroveratryloxy amide (—NHNvoc), as a 2-trimethylsilylethyloxy amide (—NHTeoc), as a 2,2,2-trichloroethyloxy amide (—NHTroc), as an allyloxy amide (—NHAlloc), as a 2-(phenylsulfonyl)ethyloxy amide (—NHPsec); or, in suitable cases (e.g., cyclic amines), as a nitroxide radical.

For example, a carboxylic acid group may be protected as an ester or an amide, for example, as: a benzyl ester; a t-butyl ester; a methyl ester; or a methyl amide.

For example, a thiol group may be protected as a thioether (—SR), for example, as: a benzyl thioether; or an acet-amidomethyl ether (—SCH$_2$NHC(=O)CH$_3$).

Combination Therapy

In certain embodiments, the invention relates to a method of co-administering a compound of Formula I and at least one other therapeutic agent. The compound and other therapeutic agent may be administered simultaneously or sequentially. When the other therapeutic agents are administered simultaneously they can be administered in the same or separate formulations, but are administered at the same time. The other therapeutic agents are administered sequentially with one another and with the compounds, when the administration of the other therapeutic agents and the compounds is temporally separated. The separation in time between the administration of these compounds may be a matter of minutes or it may be longer. Other therapeutic agents include but are not limited to anti-viral vaccines and anti-viral agents. In some instances the inhibitors are administered with multiple therapeutic agents, i.e., 2, 3, 4 or even more different anti-viral agents.

An anti-viral vaccine is a formulation composed of one or more viral antigens and one or more adjuvants. The viral antigens include proteins or fragments thereof as well as whole killed virus. Adjuvants are well known to those of skill in the art.

Antiviral agents are compounds that prevent infection of cells by viruses or replication of the virus within the cell.

There are many fewer antiviral drugs than antibacterial drugs because viruses are more dependent on host cell factors than bacteria. There are several stages within the process of viral infection which can be blocked or inhibited by antiviral agents. These stages include, attachment of the virus to the host cell (immunoglobulin or binding peptides), membrane penetration inhibitors, e.g. T-20, uncoating of the virus (e.g. amantadine), synthesis or translation of viral mRNA (e.g. interferon), replication of viral RNA or DNA (e.g. nucleotide analogues), maturation of new virus proteins (e.g. protease inhibitors), and budding and release of the virus.

Nucleotide analogues are synthetic compounds that are similar to nucleotides, but which have an incomplete or abnormal deoxyribose or ribose group. Once the nucleotide analogues are in the cell, they are phosphorylated, producing the triphosphate formed which competes with normal nucleotides for incorporation into the viral DNA or RNA. Once the triphosphate form of the nucleotide analogue is incorporated into the growing nucleic acid chain, it causes irreversible association with the viral polymerase and thus chain termination. Nucleotide analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, zidovudine (azidothymidine), imiquimod, and resimiquimod.

The interferons are cytokines that are secreted by virus-infected cells as well as immune cells. The interferons function by binding to specific receptors on cells adjacent to the infected cells, causing the change in the cell which protects it from infection by the virus. $\alpha$- and $\beta$-interferon also induce the expression of Class I and Class II MHC molecules on the surface of infected cells, resulting in increased antigen presentation for host immune cell recognition. $\alpha$- and $\beta$-interferons are available as recombinant forms and have been used for the treatment of chronic hepatitis B and C infection. At the dosages which are effective for anti-viral therapy, interferons have severe side effects such as fever, malaise and weight loss.

Anti-viral agents that may be useful in the methods of the invention include but are not limited to immunoglobulins, amantadine, interferons, nucleotide analogues, and other protease inhibitors (other than the papain-like cysteine protease inhibitors—although combinations of papain-like cysteine protease inhibitors are also useful). Specific examples of anti-viral agents include but are not limited to Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

Immunoglobulin therapy is used for the prevention of viral infection. Immunoglobulin therapy for viral infections is different than bacterial infections, because rather than being antigen-specific, the immunoglobulin therapy functions by binding to extracellular virions and preventing them from attaching to and entering cells which are susceptible to the viral infection. The therapy is useful for the prevention of viral infection for the period of time that the antibodies are present in the host. In general there are two types of immunoglobulin therapies, normal immunoglobulin therapy and hyper-immunoglobulin therapy. Normal immune globulin therapy utilizes an antibody product which is prepared from the serum of normal blood donors and pooled. This pooled product contains low titers of antibody to a wide range of human viruses, such as hepatitis A, parvovirus, enterovirus (especially in neonates). Hyper-immune globulin therapy utilizes antibodies which are prepared from the serum of individuals who have high titers of an antibody to a particular virus. Those antibodies are then used against a specific virus. Another type of immunoglobulin therapy is active immunization. This involves the administration of antibodies or antibody fragments to viral surface proteins.

Pharmaceutical Compositions

The invention provides pharmaceutical compositions for use in treating or preventing viral infections in vitro or in vivo. In one aspect, the invention provides pharmaceutically acceptable compositions which comprise a therapeutically-effective amount of one or more of the compounds described above, formulated together with one or more pharmaceutically acceptable carriers (additives) and/or diluents. In another aspect, the agents of the invention can be administered as such, or administered in mixtures with pharmaceutically acceptable carriers and can also be administered in conjunction with other agents. Conjunctive therapy thus includes sequential, simultaneous and separate, or co-administration of one or more compound of the invention, wherein the therapeutic effects of the first administered has not entirely disappeared when the subsequent compound is administered.

As described in detail below, the pharmaceutical compositions of the invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

As set out above, in certain embodiments, agents of the invention may be compounds containing a basic functional group, such as amino or alkylamino, and are, thus, capable of forming pharmaceutically-acceptable salts with pharmaceutically-acceptable acids. These salts can be prepared in situ in the administration vehicle or the dosage form manufacturing process, or through a separate reaction of a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like (see, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the invention may be compounds containing one or more acidic functional groups and, thus, are capable of forming pharmaceutically-acceptable salts with pharmaceutically-acceptable bases. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The formulations of the compounds of the invention may be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the agent which produces a therapeutic effect.

In certain embodiments, a formulation of the invention comprises an excipient, including, but not limited to, cyclodextrins, liposomes, micelle forming agents, e.g., bile acids, and polymeric carriers, e.g., polyesters and polyanhydrides; and an agent of the invention. In certain embodiments, an aforementioned formulation renders orally bioavailable an agent of the invention.

Methods of preparing these formulations or compositions may include the step of bringing into association a compound of the invention with the carrier and, optionally, one or more accessory ingredients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention as an active ingredient. A compound of the invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. Compositions of the invention may also be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

Exemplary formulations comprising agents of the invention are determined based on various properties including, but not limited to, chemical stability at body temperature, functional efficiency time of release, toxicity and optimal dose.

The preparations of the invention may be given orally, parenterally, topically, or rectally. They are of course given in forms suitable for each administration route. For example, they are administered in tablets or capsule form, by injection, inhalation, eye lotion, ointment, suppository, administration by injection, infusion or inhalation; topical by lotion or ointment; and rectal by suppositories.

Regardless of the route of administration selected, the compounds of the invention, which may be used in a suitable hydrated form, and/or the pharmaceutical compositions of the invention, are formulated into pharmaceutically-acceptable dosage forms by conventional methods known to those of skill in the art.

EXAMPLES

The invention now being generally described, it will be more readily understood by reference to the following, which is included merely for purposes of illustration of certain aspects and embodiments of the invention, and is not intended to limit the invention.

Example 1—DENV Replication in Cell Lines Lacking Abl Kinase Activity

Figure 3:
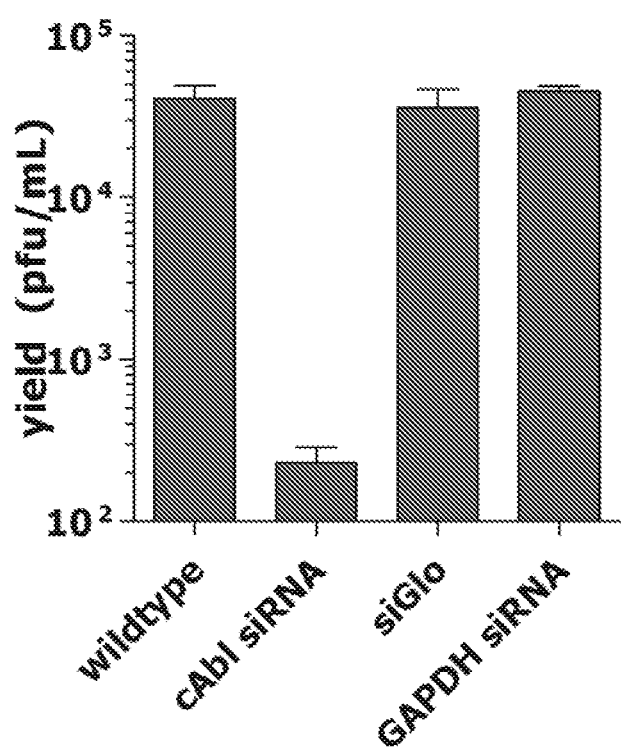
FIG. 3 depicts that DENV replication is reduced in cell lines lacking Abl kinase activity.

RNAi was used to deplete cells of c-Abl kinase. Knockout cell lines were also investigated. Cells depleted of c-Abl kinase, or mouse embryonic fibroblast (MEF) cells deficient in Abl kinase, showed a significant reduction in viral yield. See FIGS. 2 and 3.

Example 2—Reduction of Viral Titer by Kinase Inhibitors

Figure 4:
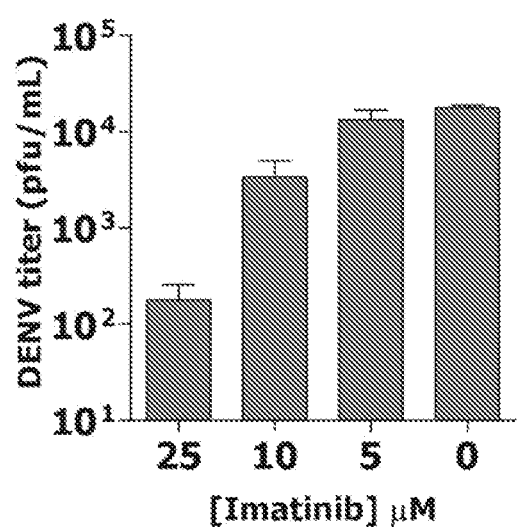
FIG. 4 depicts the reduction in DENV viral titer by imatinib.
Figure 4:
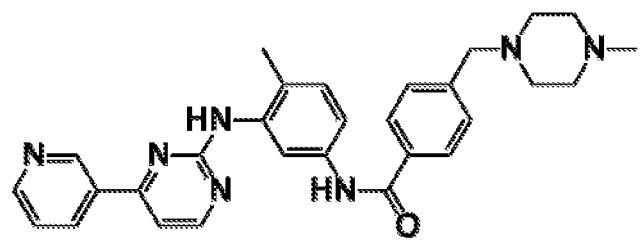

GNF2 reduced titers by over 1 log unit, while imatinib did not. See FIG. 4 and FIG. 5. The $IC_{50}$ (kinase) for imatinib was 190±6 nM and for GNF2 was 138±5 nM. The $EC_{90}$ (dengue virus serotype 2, DENV2) for imatinib was 10 μM and about 1 μM for GNF2. GNF2 is monoselective for Abl family kinases, indicating that GNF2 has an additional antiviral target.

Example 3—Order of Addition Experiments

Figure 6:
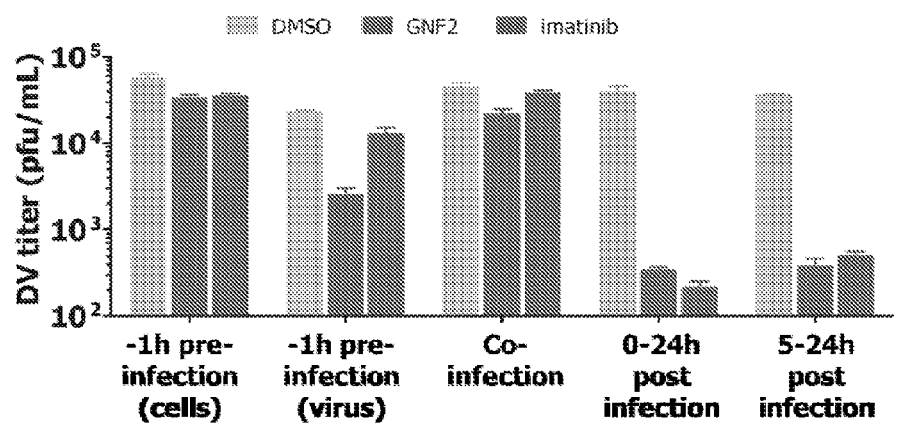
FIG. 6 depicts the results from Example 3 (DMSO=left bar; GNF=middle bar; and imatinib=right bar).

In order to investigate the role of kinases on DENV entry, the order of addition of the cells, virus, and inhibitor was investigated. An inhibitor was either (i) contacted with a virus for 1 h at 37° C.; (ii) contacted with cells for 1 h at 37° C.; or (iii) contacted with a virus and cells for 1 h at 37° C. The cells were washed to remove virus and inhibitor. The washed cells were exposed to either DMSO or an inhibitor. Viral titer was measured at intervals post-infection by harvesting supernatants and measuring virus production by a plaque formation assay (PFA). The data indicate that GNF-2 is active prior to viral entry while imatinib and GNF2 share a post-entry antiviral activity. See FIG. 6.

Example 4—Investigation of Post-Entry Role of Abl Kinases

Imatinib does not lower DV titer when pre-incubated with the virus as compared to a DMSO control. However, treatment of the virus with either a quinazoline entry inhibitor (see Wang, Q.-Y., et al. *Antimicrob. Agents Chemother.* 2009, 53(5), 1823-1831) or GNF-2 significantly lowers titer by ~1 log. Post-treatment of cells with either Abl kinase inhibitor significantly reduces titer as well. Data not shown.

In short, GNF-2 acts at two separate and distinct steps of DV life cycle to inhibit DENV.

Example 5—SAR

Figure 7:
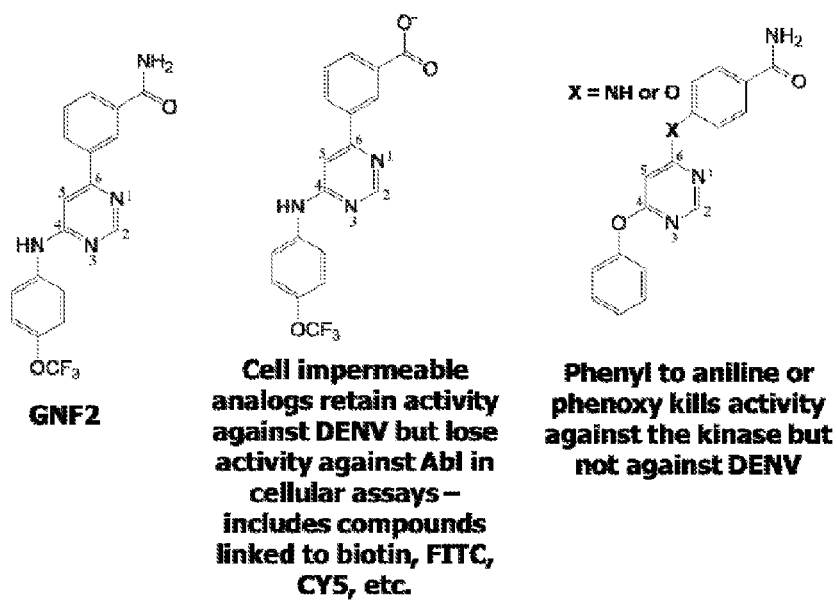
FIGS. 7-9 depicts GNF2 and various GNF2 analogs. The activities of these compounds indicate that kinase- and virion-mediated activities are separate.
Figure 8:
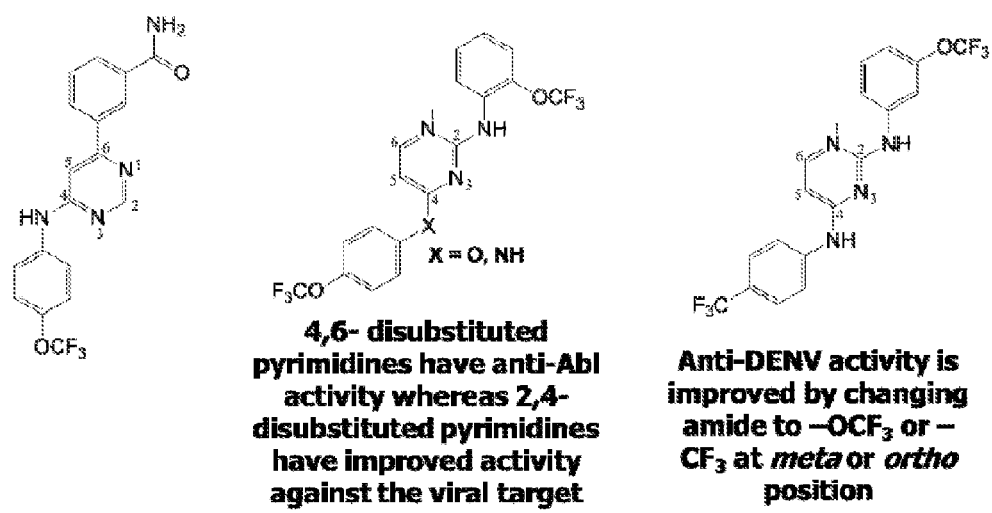
Figure 9:
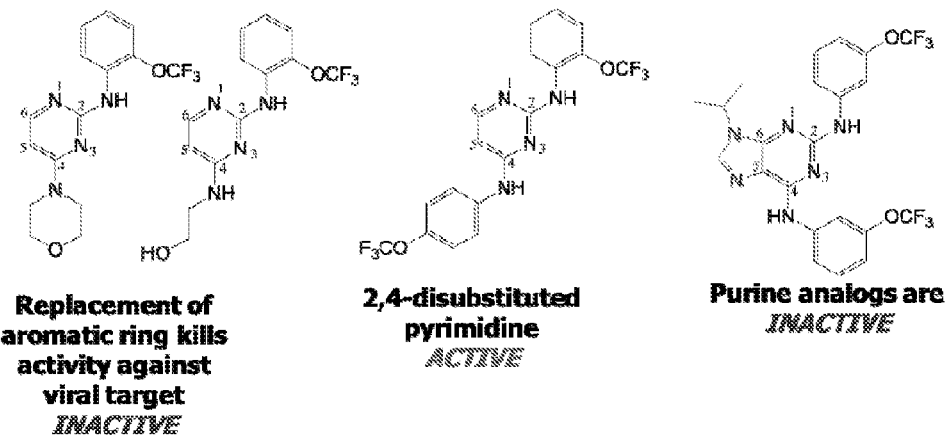

See FIG. 7, FIG. 8, and FIG. 9.

About 90 GNF2 analogs were synthesized and screened. Twenty-three small molecules were identified that inhibit DENV and have no measurable activity against Abl kinases. The most potent inhibitors of DENV entry had $EC_{90}$ values of 1-15 μM against all four dengue serotypes.

Example 6—Biotinylation of Inhibitor

Figure 10:
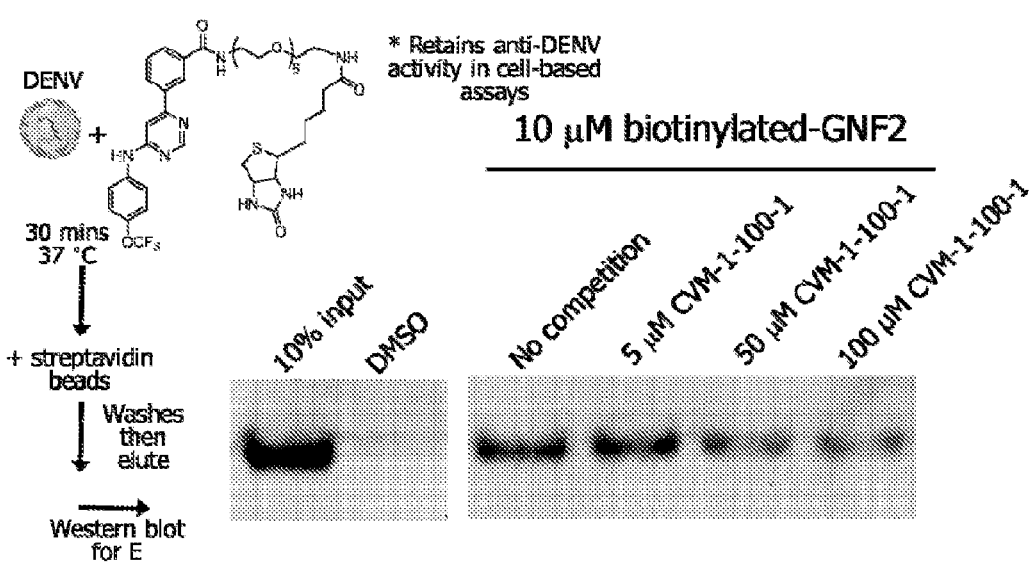
FIG. 10 depicts an assay investigating the pulldown of purified virus with biotinylated GNF2.
Figure 11:
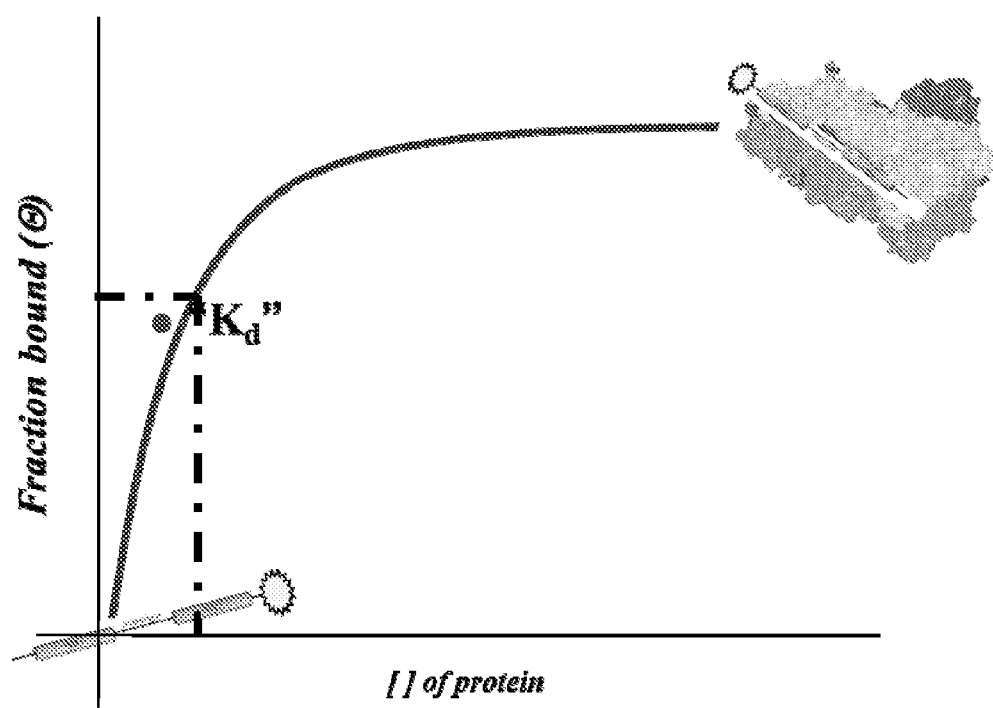
FIG. 11 depicts a schematic showing the experimental setup for a fluorescence polarization assay to measure binding of GNF2 to DENV E protein. Binding of GNF2-FITC (GNF2-fluorescein isothiocyanate) by E dimer decreases rate of tumbling and increases polarization of the emitted fluorescence.
Figure 12:
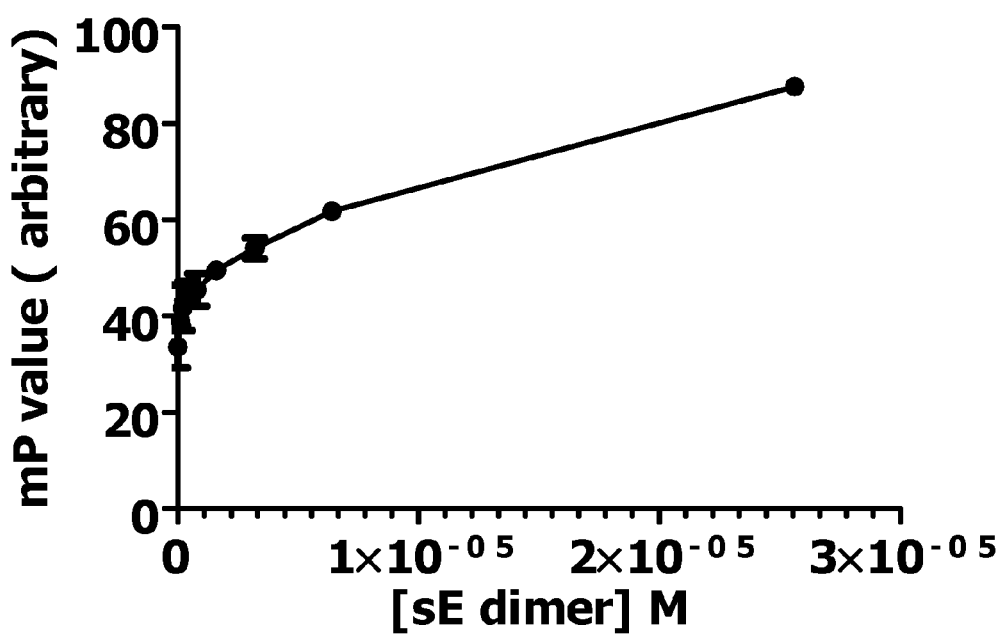
FIG. 12 depicts the detection of binding of GNF2-FITC to recombinant DENV sE prefusion dimer by fluorescence polarization.

Biotinylated GNF2 was incubated with virus for 45 min at 37° C., then the competing compound was added for an additional 45 min. See FIG. 10. No pulldown of vesicular stomatitis virus (VSV) was observed. Importantly, biotinylated GNF2 retains anti-DENV activity in cell-based assays.

Example 7—Use of Fluorescent Microscopy to Track GNF2-CY5 During DENV Entry

Figure 13:
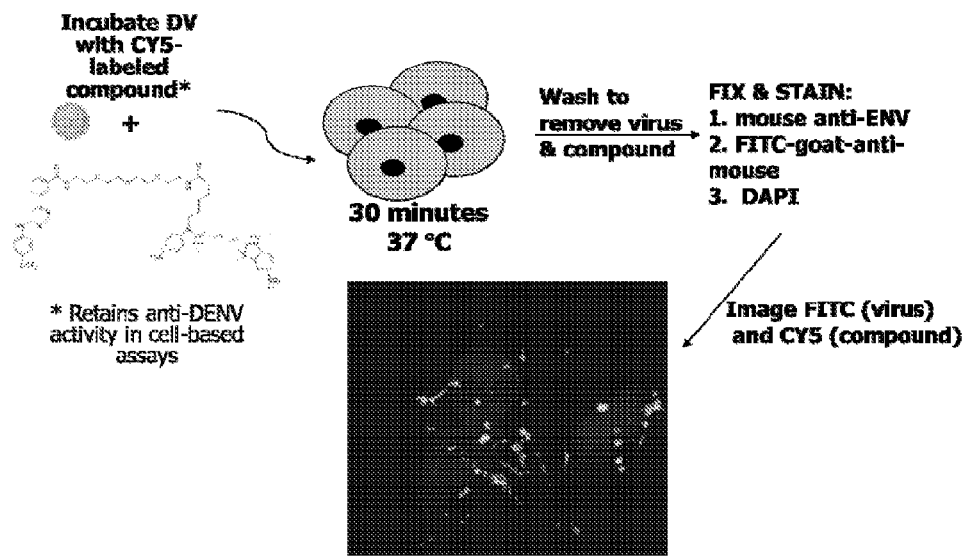
FIG. 13 depicts the use of fluorescent microscopy to track GNF2-CY5 during DENV entry. GNF2-CY5 retains its antiviral activity as compared to GNF2.

Fluorescent microscopy was used to track uptake of inhibitors during viral entry. See FIG. 13. Importantly, GNF2-CY5 retains its antiviral activity against DENV serotype 2 as compared to GNF2.

These studies showed that GNF2-CY5 was not taken up in the absence of DENV2 (data not shown). Also, GNF2-CY5 co-localized with the DENV2 E protein (data not shown). Finally, since GNF2 reduced DENV titers in cell-based assays, the mechanism of inhibition is not that the compounds block attachment or uptake of the virus.

Example 8—Effect of Kinase Inhibitors on DENV Fusion

Figure 14:
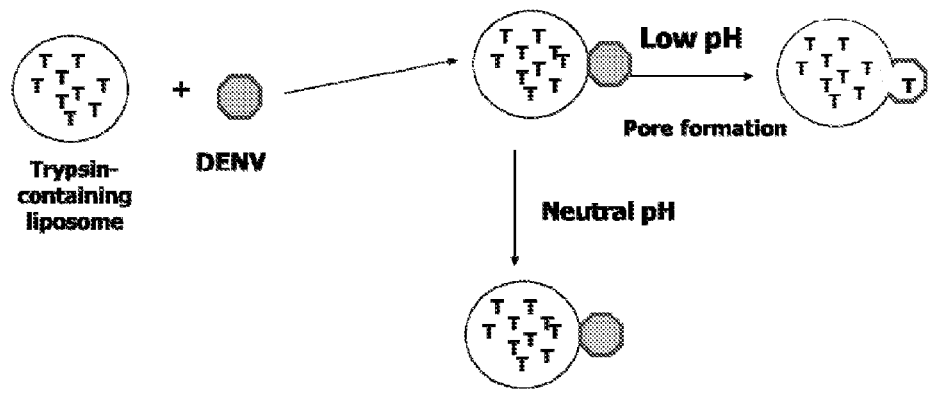
FIG. 14 depicts a schematic representation of the interaction between DENV and a liposome.
Figure 15:
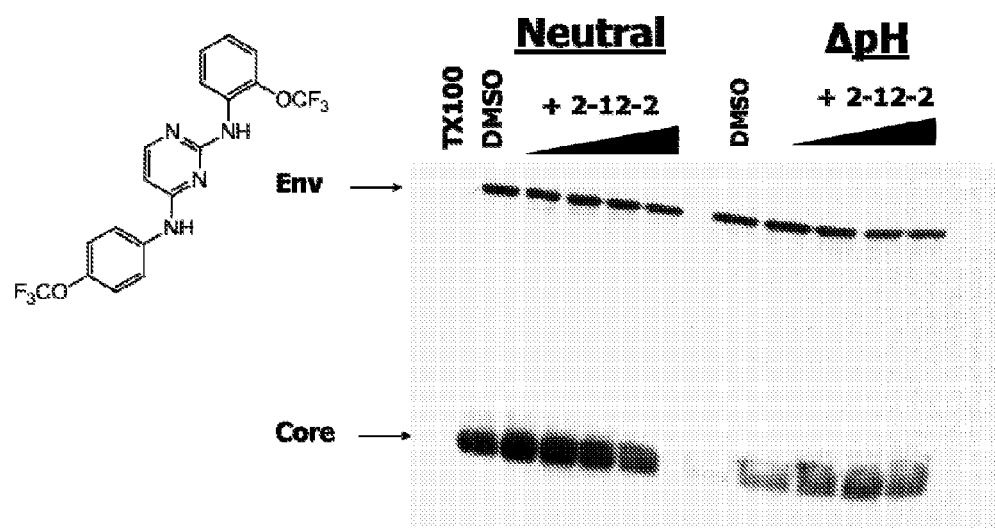
FIG. 15 depicts an assay of DENV fusion in the presence or absence of a compound of the invention.

A capsid protection assay was used to measure fusion pore formation and content mixing of DENV2 with liposomes. See FIG. 14. Our data indicate that DENV2 cannot complete fusion in the presence of the inventive inhibitors. See FIG. 15.

Figure 16:
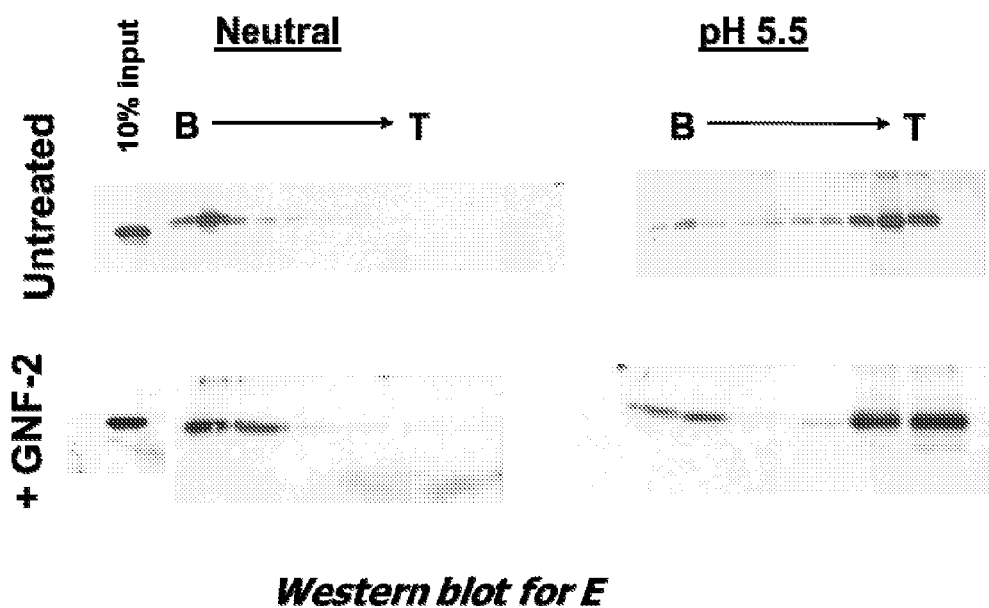
FIG. 16 depicts an assay indicating that GNF2 does not block association of DENV with liposomes.
Figure 17:
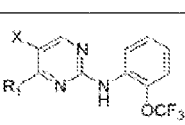
Figure 17:
Figure 17:
Figure 17:
Figure 17:
Figure 17:
Figure 17:
Figure 17:
Figure 17:
Figure 17:
Figure 17:
Figure 17:
Figure 18:
Figure 18:
Figure 18:
Figure 18:
Figure 18:
Figure 18:
Figure 18:
Figure 20:
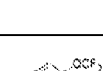
Figure 20:
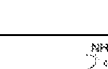
Figure 20:
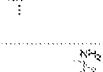
Figure 20:
Figures 21, 22:
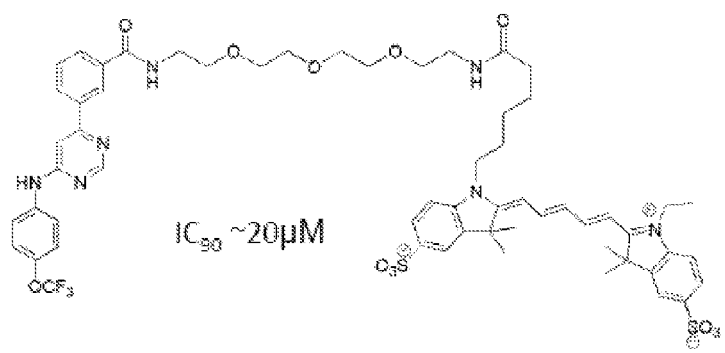
Figure 23:
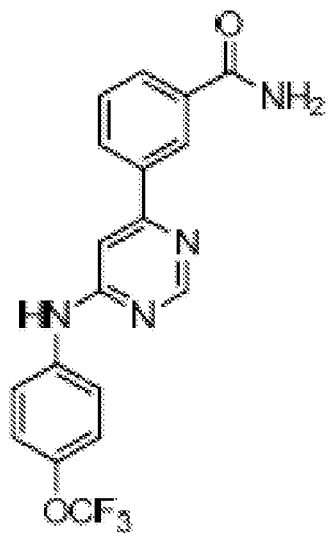
Figure 24:
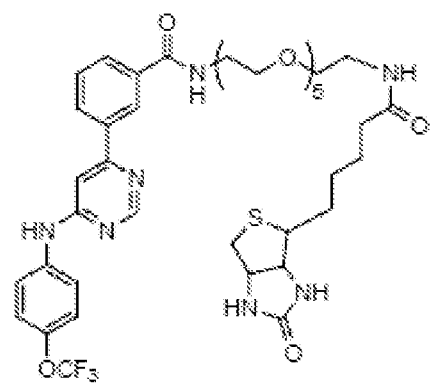
Figure 25:
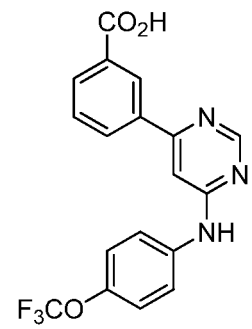
Figure 26:
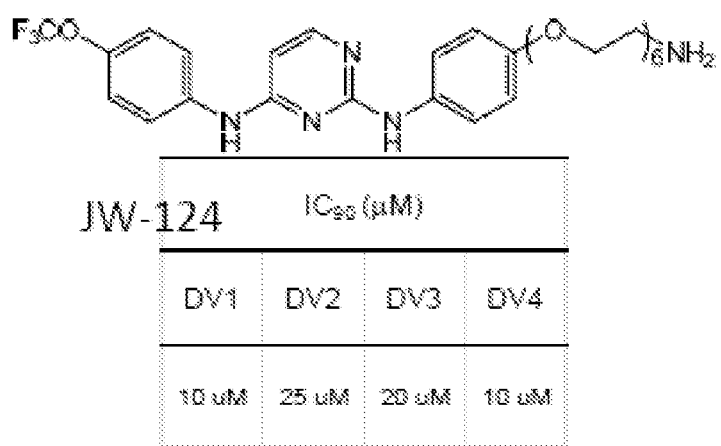
Figure 27:
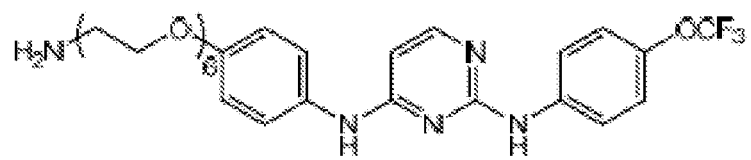
Figure 28:
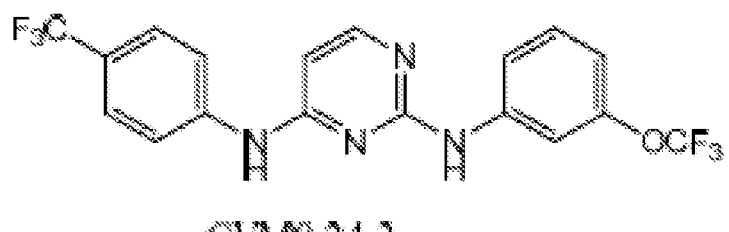
Figure 32:
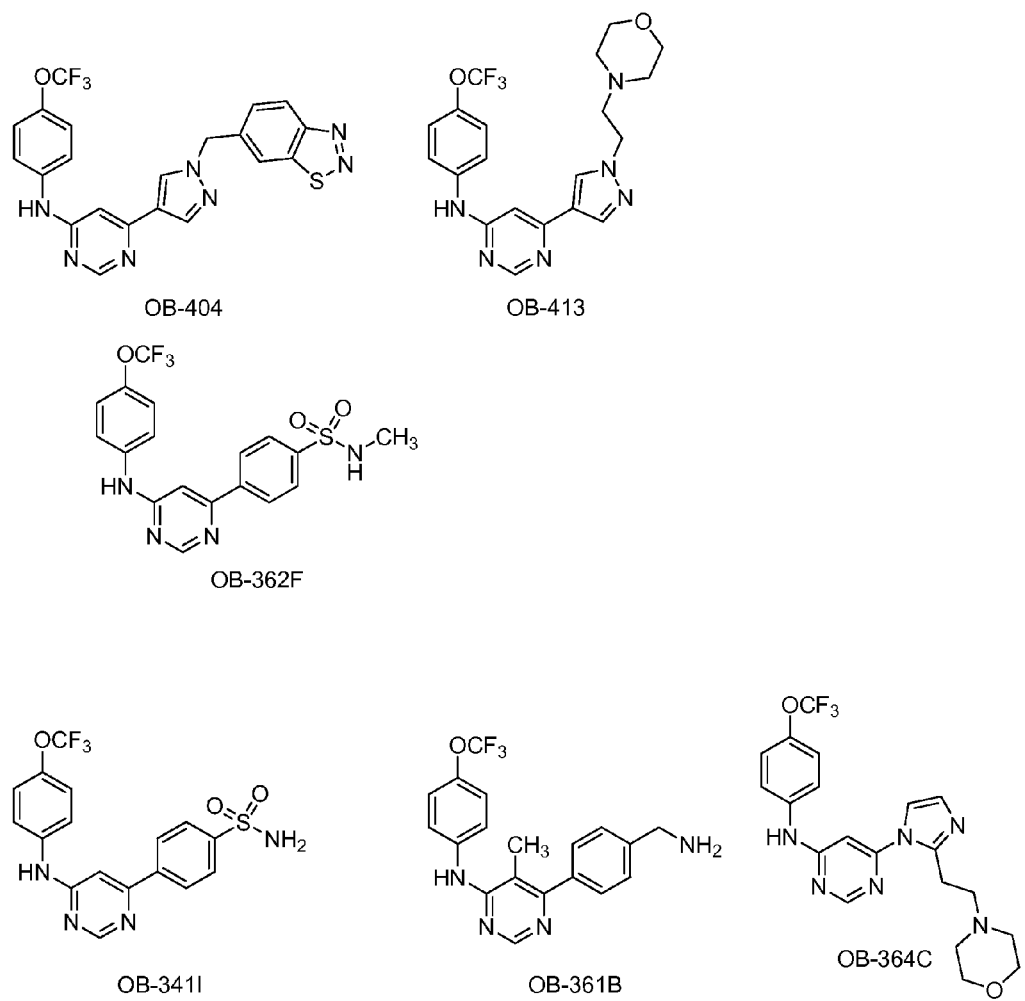
FIG. 32 depicts various 4,6-disubstituted compounds of the invention.
Figure 33:
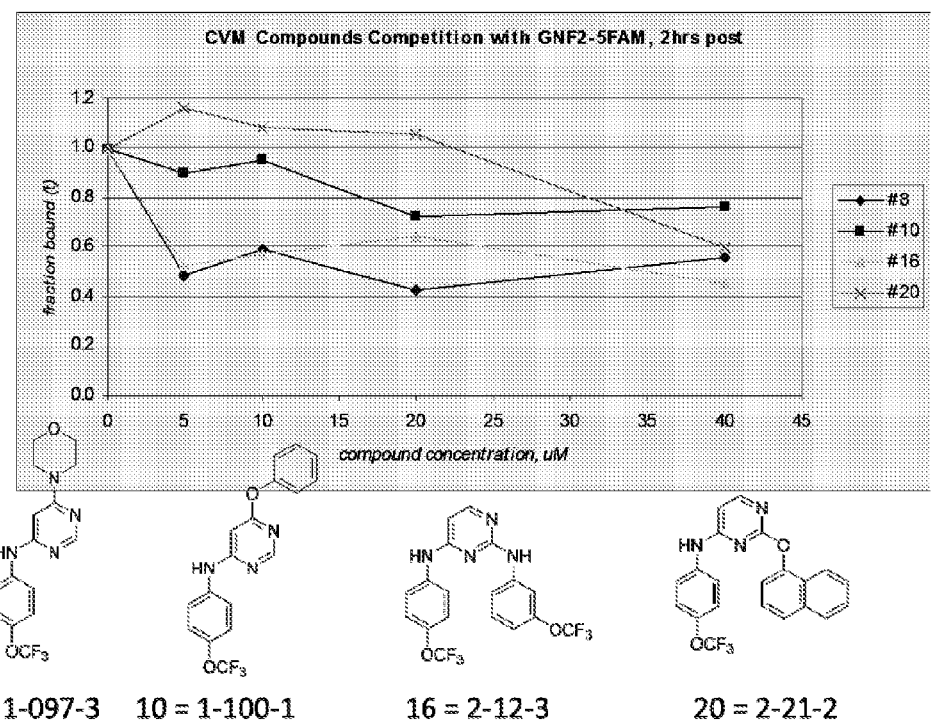
FIGS. 33 and 34 depict fluorescence polarization data showing that the 2,4-disubstituted compounds compete with GNF2-FITC for binding to E. The competition is complete by 2 h (FIG. 33) for the 4,6-disubstituted derivatives (1-100-1, 1-97-3) but takes until 12 h (FIG. 34) for the 2,4-disubstituted compounds (2-12-3, 2-21-2).
Figure 34:
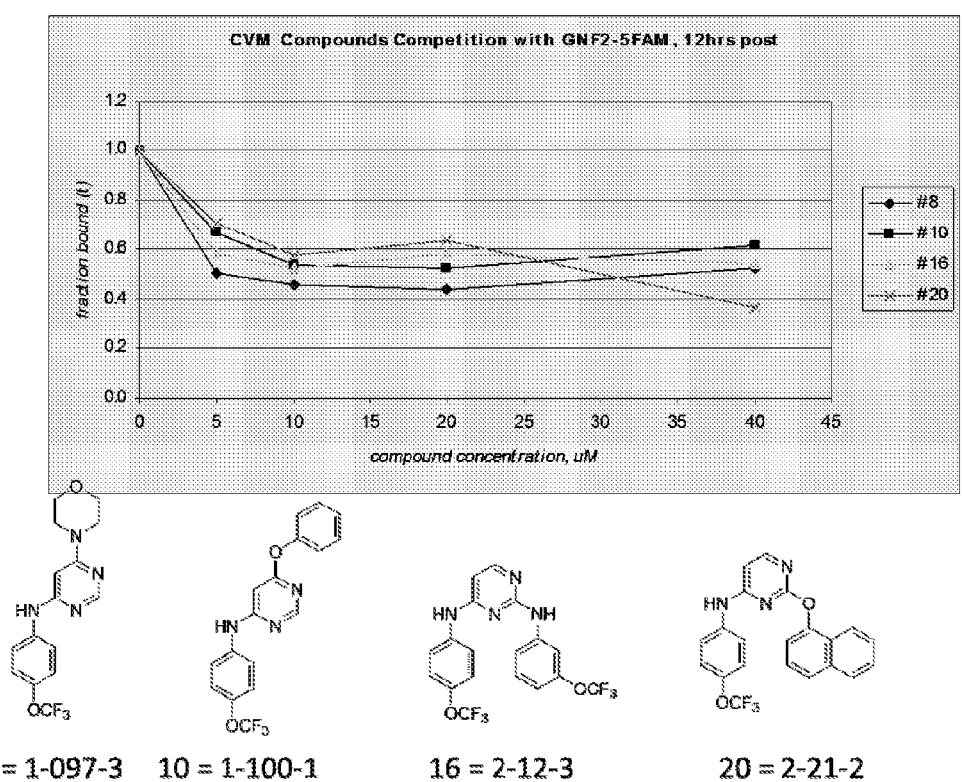
Figure 35:
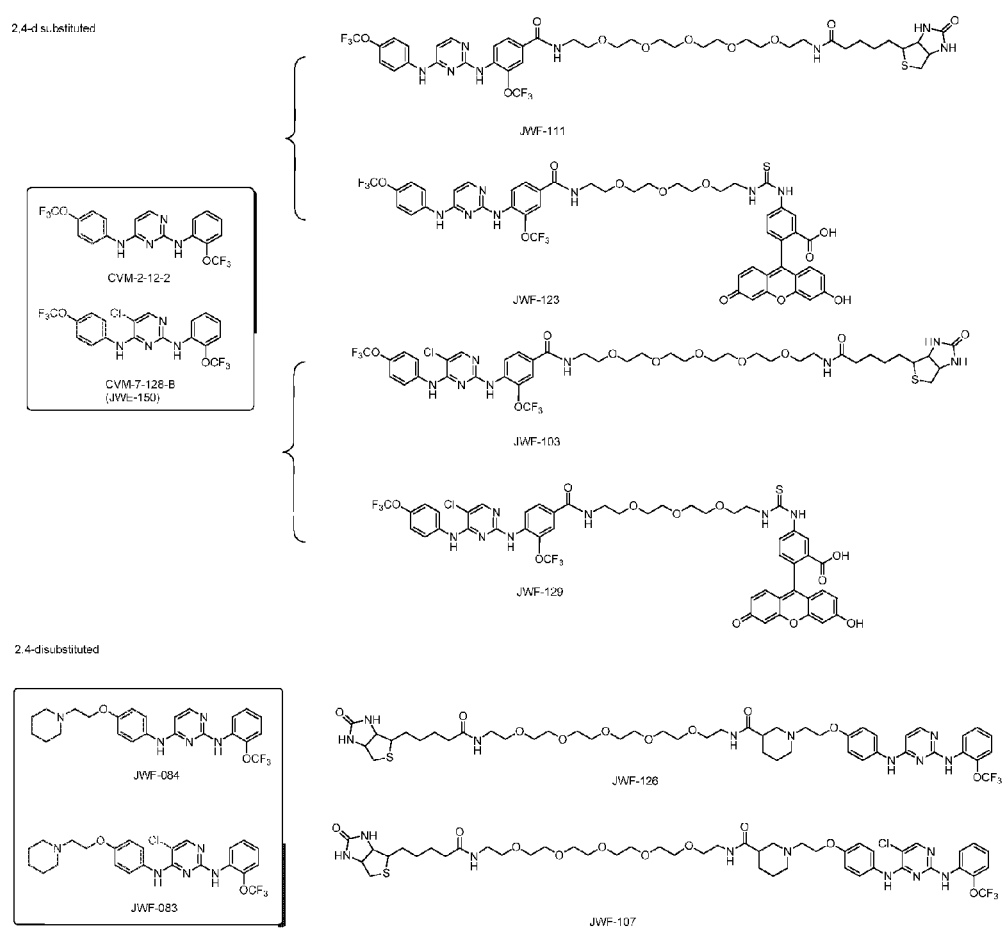
FIGS. 35 and 36 depict compounds of the invention comprising biotin, FITC, or BoDIPY functionality.
Figure 36:
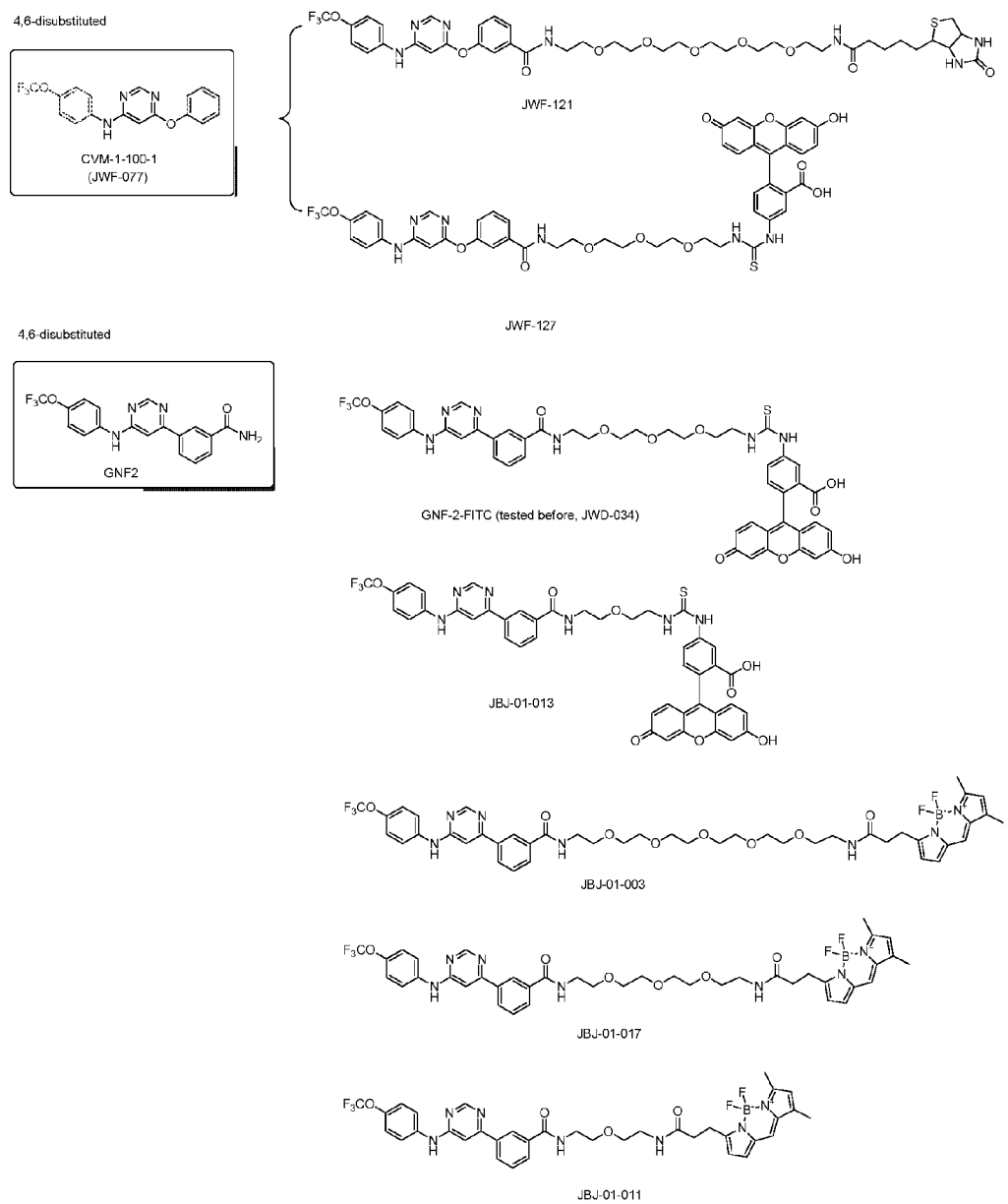
Figure 37:
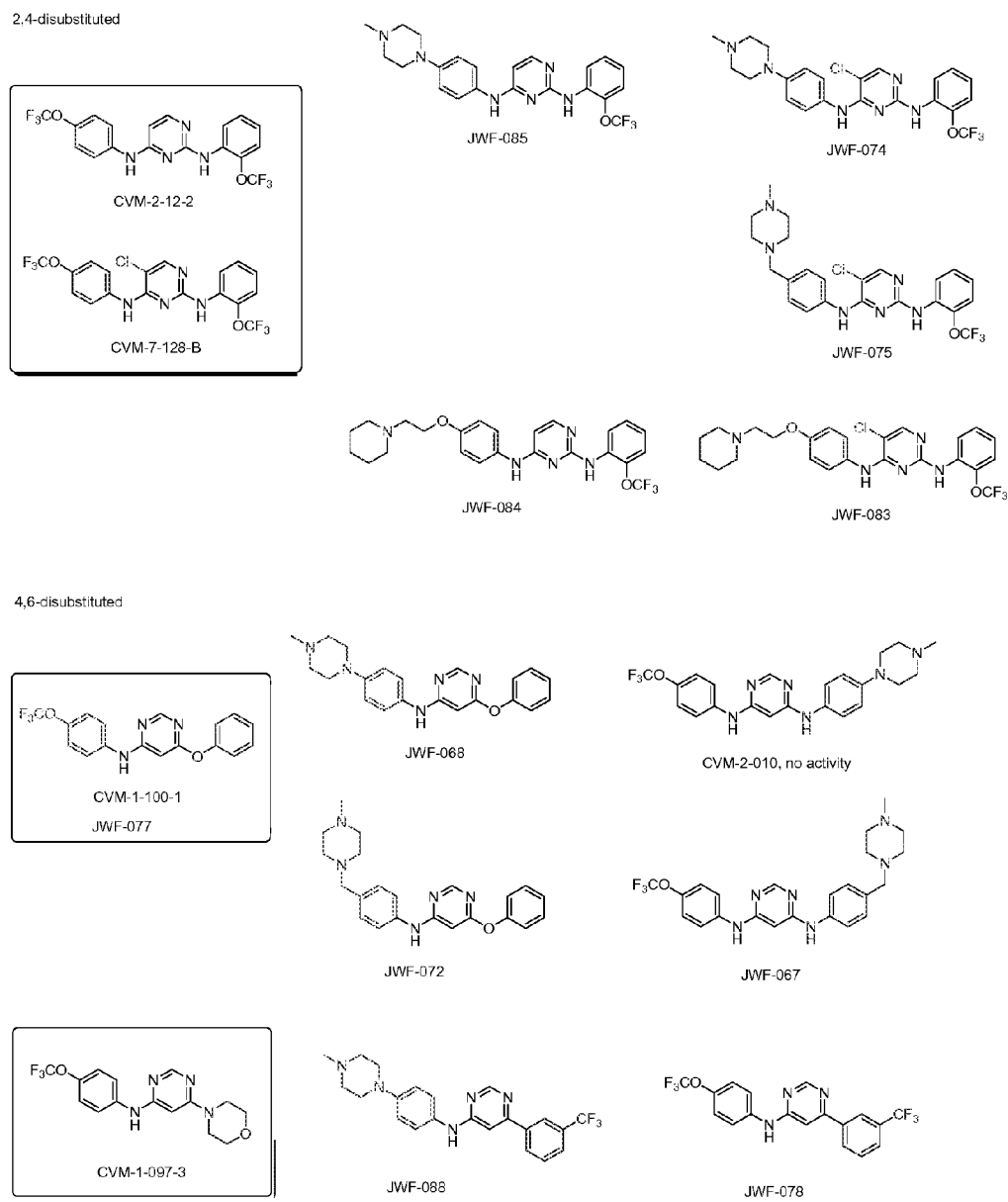
FIG. 37 depicts compounds of the invention comprising a solubility-enhancing group.
Figures 38, 39:
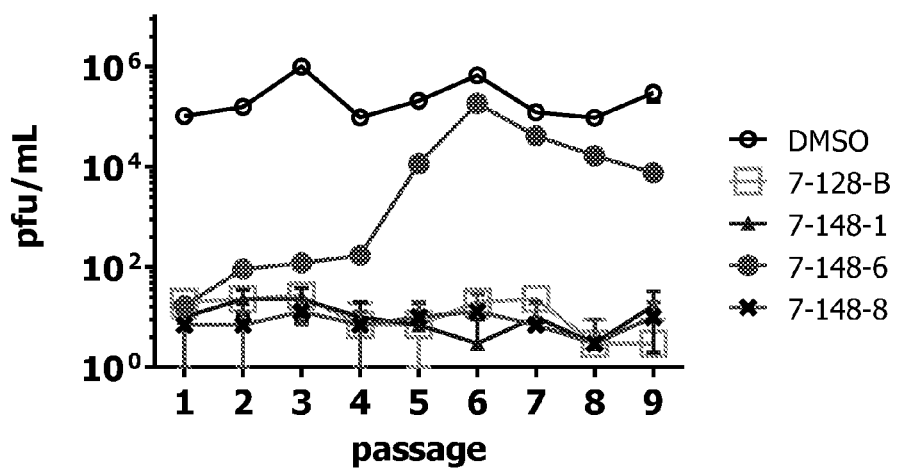
FIG. 38 tabulates the EC90, IC50, and KD concentrations for various compounds of the invention (see FIGS. 35-37). All EC90 and KD values were measured against dengue serotype 2 (DENV2).
FIG. 39 depicts viral titer as a function of number of passages, which was used in the selection of a mutant resistant to various compounds.

In addition, the data indicate that an inventive compound does not block association of DENV with liposomes. See FIG. 16.

Example 9—General Methods

Compounds were synthesized and purified by established methods to generate multiple series of regioisomeric 4,6- and 2,4-disubstituted pyrimidines. To make focused changes to the 4,6-disubstituted core structure of GNF-2 while holding either the 4-trifluoromethoxy aniline or the aryl benzamido portions constant, 4,6-dichloropyrimidine was first mono-derivatized either under basic amination conditions or under Suzuki reaction conditions to prepare mono-substituted pyrimidine intermediates. The two resulting intermediates were subsequently reacted with amines, phenols or anilines in a nucleophilic substitution reaction under various optimized conditions to afford final compounds in good yields. Regioisomeric 2,4-disubstituted pyrimidines were prepared in parallel via an analogous synthetic route by holding the C4 position of the pyrimidine constant with a 4-trifluoromethoxy aniline or a 3-aryl benzamide and varying the C2 substituents. The compounds were then screened for anti-DENV activity when present at 75 μM during pre-treatment of the inoculum and the 1 hour infection period. Compounds that lowered DENV2 titer by at least one log at this concentration were then tested at 25 μM in order to determine if these compounds were more effective than c-GNF-2, our initial compound. Most of the 4,6-disubstituted analogs were inactive in reducing the viral titer. Importantly, the most potent compound in this series is structurally similar to GNF-2 but is devoid of c-Abl inhibitory activity.

In contrast to the 4,6-pyrimidine compound series, 2,4-disubstituted pyrimidine analogs yielded compounds with even greater potency in the DENV yield reduction assay. In particular, compounds with a trifluoromethoxy aniline at the C4 position of the pyrimidine ring were found to be more potent than compounds containing the aryl benzamide of the parent compound. Several compounds in this series reduced viral yields to undetectable levels under the conditions of these experiments. These data suggested that in the 2,4-pyrimidine series, the ortho- or meta-trifluoromethoxy substituted anilines at the C2 position were a favorable chemical framework for obtaining compounds that inhibited dengue virus potently.

Figure 5:
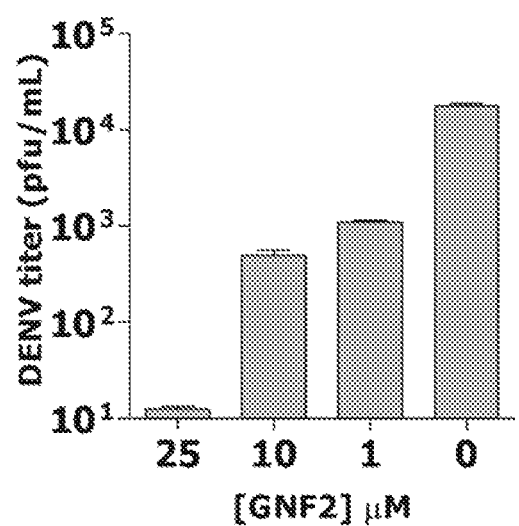
FIG. 5 depicts the reduction in DENV viral titer by GNF2.
Figure 5:
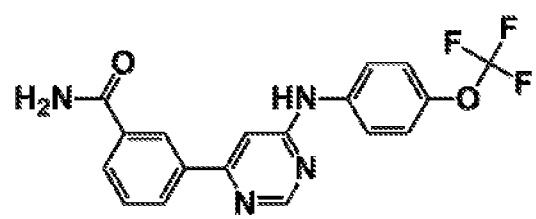

A further focused SAR study was performed by preparing analogs containing an ortho-trifluoromethoxy substituted aniline at the 2-position of the 2,4-pyrimidine ring. As the 4-position of 2,4-dichloropyrimidine is more reactive than the 2-position, various anilines and amines were first reacted with 2,4-dichloropyrimidine to prepare 4-substituted pyrimidines. The mono-aminated products were then subjected to a second amination with ortho-trifluoromethoxy aniline under acidic conditions to obtain the final products. The compounds were tested for anti-DENV activity in the viral yield assay under pre-/co-infection conditions as described above. Viral yield was reduced by 100- to 1000-fold with pyrimidines bearing an aniline at the C2 position, consistent with the previous series in which the most active compounds contained 3 aromatic rings connected through an amide or ether linkage (e.g., compounds X and Y). Compound 63 was the most potent compound in this series, causing a 3 log unit drop in viral titer at 75 µM concentration of compound. To determine the optimal position of the trifluoromethoxy group on the aniline attached at the C2 position, we compared the most active compounds with analogs in which the trifluoromethoxy aniline was moved to the meta position (FIG. 5B). While aniline substituents at the C4 position retained potent antiviral activity in the meta-series, benzyl amine substituents at the C4 position lost activity in comparison to the ortho-series where a robust 2-log unit drop in viral titter was observed. For example, compounds 65 and 66 in the meta series were less active than compounds 57 and 62 in the ortho series. To explore substitutions at the C5 position of the pyrimidine ring, we prepared a limited set of compounds (compounds 64 and 73-75, FIG. 5) and found that introduction of a chloride at the C5 position was tolerated only in the ortho series and that replacement of the pyrimidine core with a purine core resulted in a complete loss of activity (data not shown).

Example 10—GNF-2 Acts at Two Separate Parts of the DENV Infectious Cycle

To examine the point(s) in the DENV infectious cycle affected by GNF-2, we performed order of addition experiments measuring the effect of GNF-2 when incubated with cells or virus prior to infection (PRE), when added at the time of infection (CO), or when added after the initial infection had been allowed to occur (POST). To additionally probe the extent to which GNF-2's anti-DENV2 activity may be mediated by Abl kinases, we performed parallel experiments with imatinib, a well-characterized compound with comparable activity against Abl kinases in biochemical and cellular assays, but with a pharmacophore and molecular mechanism distinct from GNF-2's. GNF-2, imatinib, or DMSO was present in the viral inoculum and/or in the cell culture medium at various times during the experiment. BHK21 cells were inoculated with DENV2 at a multiplicity of infection (MOI) of 1 and incubated for one-hour at 37° C. after which the inoculum was removed, the cells were washed, and fresh medium was added to limit infection to a single round. At twenty-four hours post-infection, corresponding to approximately one complete life cycle of DENV, the yield of infectious virions that had been released to the culture supernatant was quantified by plaque-formation assay (PFA) as a measure of successful DENV replication. We observed that both GNF-2 and imatinib inhibited DENV2 replication when added directly after viral infection, and addition of either inhibitor five hours post-infection caused a comparable level of inhibition. This suggested that GNF-2 and imatinib affect events downstream of viral entry since internalization and fusion of dengue virions has been shown to occur on the order of minutes (average time 12.5 minutes) following attachment to the cell surface. In subsequent dose-response experiments, we determined that GNF-2 and imatinib have comparable inhibitory potencies against this post-entry step, with $IC_{90}$ values—defined as the concentration of compound sufficient to cause a 10-fold decrease in the single-cycle viral yield—of 8 µM observed for both compounds when added to cells post-infection.

Somewhat unexpectedly, we also observed significant inhibition of DENV2 when GNF-2 was pre-incubated with the viral inoculum prior to infection but no inhibition of DENV2 when the inoculum was pre-incubated with imatinib or when GNF-2 or imatinib were added to cells at the time of inoculation. Together, these observations suggested that this anti-DENV2 activity may be due to a target present in the viral inoculum and be mediated by an Abl-independent mechanism. To quantify this effect of GNF-2 on DENV2 infectivity, we performed dose-response experiments in which the virus inoculum was pre-incubated with varying concentrations of compound at 37° C. for 45 minutes prior to inoculation of cells. The infection was permitted to proceed for one hour at 37° C. followed by washes to remove non-adsorbed virus and compound, replacement of fresh medium lacking compound, and then quantification of viral yield at 24 hours post-infection by plaque formation assay.

To further examine the idea that GNF-2 inhibits DENV2 via two separate mechanisms, one mediated by Abl kinases at a post-entry step and one mediated by an independent target relatively early in the infectious cycle, we performed additivity experiments using GNF-2, imatinib, and NITD6, a previously validated inhibitor of DENV2 entry shown to interact with the DENV2 envelope protein and found to inhibit DENV2 infectivity in our assay with an $EC_{90}$ value of 200 nM. As expected, additive inhibitory effects were observed when pre-treatment of the inoculum with NITD6 was combined with treatment of DENV2-infected cells with imatinib. These additive anti-DENV activities were recapitulated by pre-incubation of the inoculum with GNF-2 and post-incubation of DENV2-infected cells with GNF-2, suggesting that GNF-2 inhibits DENV2 via two distinct mechanisms. Since GNF-2's activity as an Abl kinase inhibitor has been well-documented, we next focused on studying the target and mechanism responsible for its activity as an inhibitor of DENV2 infectivity.

Example 11—GNF-2 Interacts Directly with the Dengue Virus Virion

Since GNF-2's effect on DENV2 infectivity required its pre-incubation with the virus inoculum prior to infection, we hypothesized that GNF-2 might target the dengue virion directly. To explore this hypothesis, we synthesized a derivative in which the exocyclic amide of GNF-2 is connected via a polyethylene glycol linker to biotin. The resulting compound, biotin-GNF-2 was found to inhibit DENV2 in the infectivity assay with an $EC_{90}$ value (~18 µM), comparable to that of the parental GNF-2. Additionally, the KD of GNF2-biotin for DENV2 soluble perfusion E is around 1 µM. See FIGS. 35-38.

Purified DENV2 virions were incubated with biotin-GNF-2 at 37° for 45 minutes after which the reaction mixture was mixed with streptavidin beads for affinity capture of biotin-GNF-2. The streptavidin beads were washed ten times to remove non-specifically bound material and then boiled in SDS buffer. Western blot analysis of the SDS buffer eluate for the presence of the DENV2 E protein demonstrated affinity capture of the DENV2 E protein that was dependent on the presence of biotin-GNF-2. Parallel negative control experiments performed with purified particles of vesicular stomatitis virus (VSV), an enveloped, negative-sense RNA virus, showed no capture of this unrelated virus and demonstrated that the biotin-GNF-2-mediated affinity capture of viral particles was specific for DENV2. Competition with compound 1-100-1 demonstrates that the interaction of virions with biotin-GNF2 is reversible and that the association is not simply aggregation.

This experiment demonstrates a direct interaction with virions; the location of the interaction and the binding affinity are investigated in Examples 12 and 13.

Example 12—Measurement of Binding Affinity Between GNF-2 and Dengue Virus Envelope Protein by OCTET RED384

Figure 42:
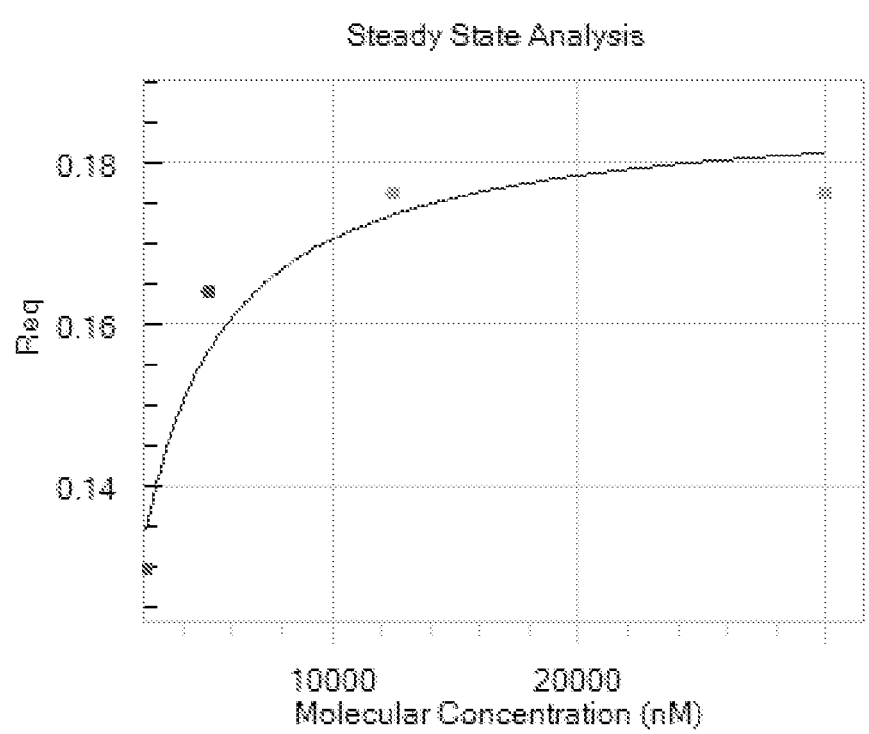
FIG. 42 depicts the KD of DENV2 $sE_2$(wt) to GNF2-biotin.
Figure 43:
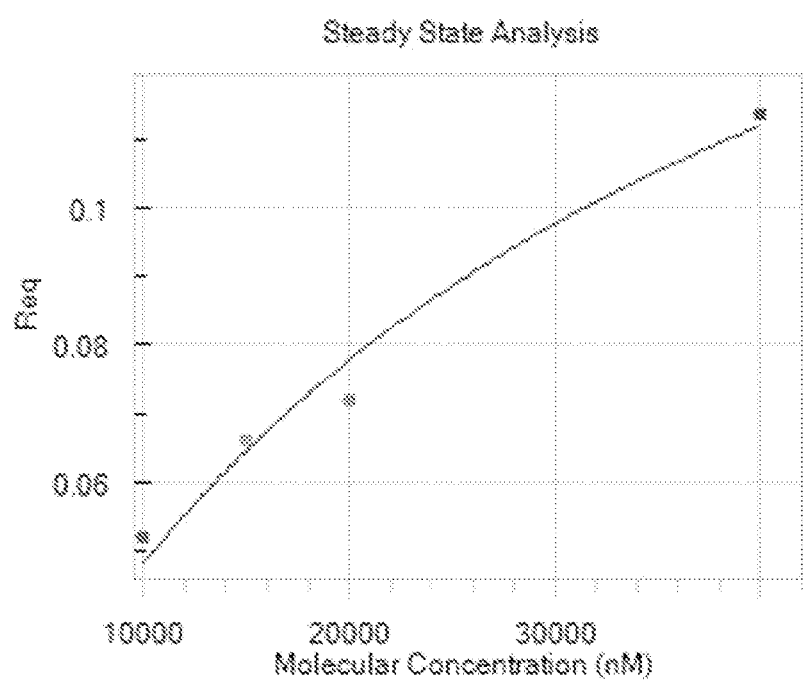
FIG. 43 depicts the KD of DENV2 $sE_2$(M196V) to GNF2-biotin.

Using recombinantly expressed, soluble form of the prefusion E dimer (sE$_2$), we performed equilibrium affinity measurements. Octet RED384 and streptavidin biosensors (from Fortebio) was used for binding affinity studies. Streptavidin biosensor tips were hydrated in loading buffer (1×PBS, pH 7.4 with, 2% DMSO) for at least 10 min at room temperature. SA tips were saturated with 0.5 μM biotinylated-GNF2 or DMSO (as control) for in 5-10 min and then quenched by 10 μg/mL Biocytin in 2 min. The biosensor then were equilibrated in running buffer (1×PBS, pH 7.4 with, 2% DMSO, 0.1% BSA and 0.02% Tween 20) for 10 min before collecting baseline in running buffer. Association of sE(wt) or sE(M196V) mutant to biotinylated compounds were measured at minimum four protein concentrations from 2 μM to 30 μM in 10-20 min and dissociation were followed by dipping the biosensor into running buffer in 10 min. The data were analyzed by ForteBio software for, global fitting and steady state kinetics. KDs were obtained from steady state kinetics analysis. See FIG. 42 and FIG. 43.

Example 13—Measurement of IC50 by Fluorescence Polarization Assay

The DV2 sE$_2$(wt) dimer or corresponding DI/DII monomer at different concentrations from 0 to 36 μM were incubated with 40 nM FITC compound in kinetics buffer (1×PBS, pH 7.4 with, 2% DMSO) in low-volume 384 well microplates at RT for 2 hours or at 4° C. for 24 hours. The fluorescence polarization measurements were recorded in a PerkinElmer EnVisions instrument (excitation wavelength, 485 nm; emission wavelength, 535 nm). The FP data were analyzed by Origin9 and fitted by dose response model.

Example 14—Selection of a Resistant Mutant

DENV2 NGC (MOI 0.1) was incubated with selected compounds for 45 minutes at 37° C. before addition to 10$^6$ Vero cells in a T25 flask. After a one hour infection, 5 mL medium was added (2% FBS in DMEM) containing compound or DMSO. Infections proceeded for four days, at which point supernatant was harvested and spun briefly to remove cell debris. Five hundred μL of supernatant was used to infect a fresh T25 of Vero for one hour, at which point 4.5 ml of medium containing compound was added. Viral titer of each passage was determined by plaque-forming assay. The first passaging with compounds maintained 20 μM of each compound over eight passages. The second passaging started at 2.5 μM and increased by 2.5 μM each passage until 20 μM was reached, which was kept constant for two passages. Consensus sequencing of the 7-148-6-resistant population identified mutation M196V in the E protein, which maps to a beta-strand at the base of the beta-octglucoside binding pocket identified in the crystal structure of the prefusion E dimer. See FIG. 39.

Figure 40:
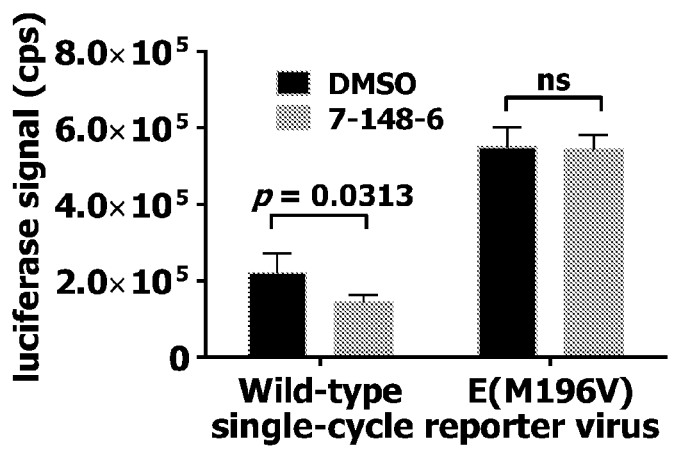
FIG. 40 depicts the confirmation that M196V mutation in DENV2 E confers decreased sensitivity to 7-148-6.

The M196V mutation was independently introduced to DENV2 E in a single-cycle reporter virus system and confirmed that it confers decreased sensitivity to 7-148-6. See FIG. 40.

Figure 41:
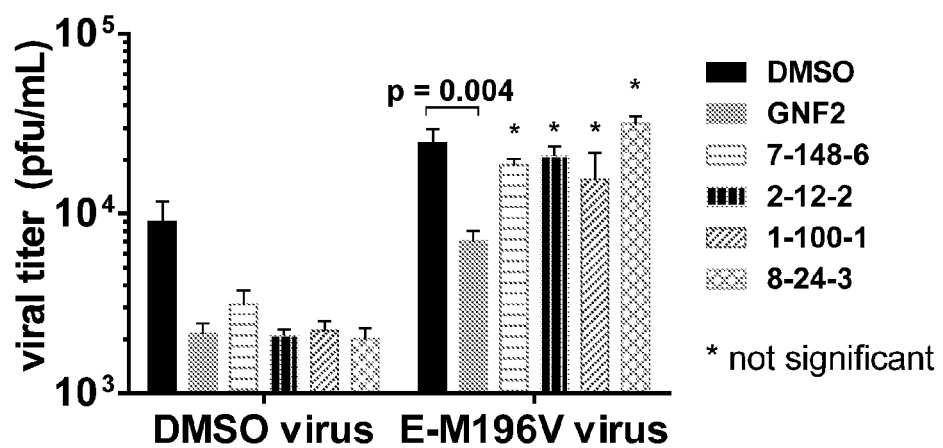
FIG. 41 depicts decreased sensitivity of DENV2 with an M196V E mutation to various compounds.

Testing of the 7-148-6-resistant DENV2 quasispecies against other disubstituted pyrimidine entry inhibitors suggested that it confers decreased sensitivity to additional members of both the 2,4-disubstituted pyrimidine series (e.g., 2-12-2, 8-24-3) and the 4,6-disubstituted pyrimidine series (e.g., 1-100-1) when compared to a DMSO-passaged control strain although the mutant appears to still be sensitive to GNF-2. See FIG. 41.

EQUIVALENTS

While specific embodiments of the subject invention have been discussed, the above specification is illustrative and not restrictive. Many variations of the invention will become apparent to those skilled in the art upon review of this specification. The appended claims are not intended to claim all such embodiments and variations, and the full scope of the invention should be determined by reference to the claims, along with their full scope of equivalents, and the specification, along with such variations.

All publications and patents mentioned herein are hereby incorporated by reference in their entirety as if each individual publication or patent was specifically and individually indicated to be incorporated by reference. In case of conflict, the present application, including any definitions herein, will control.

We claim:

1. A compound, or a pharmaceutically acceptable salt thereof, wherein the compound is selected from the group consisting of:

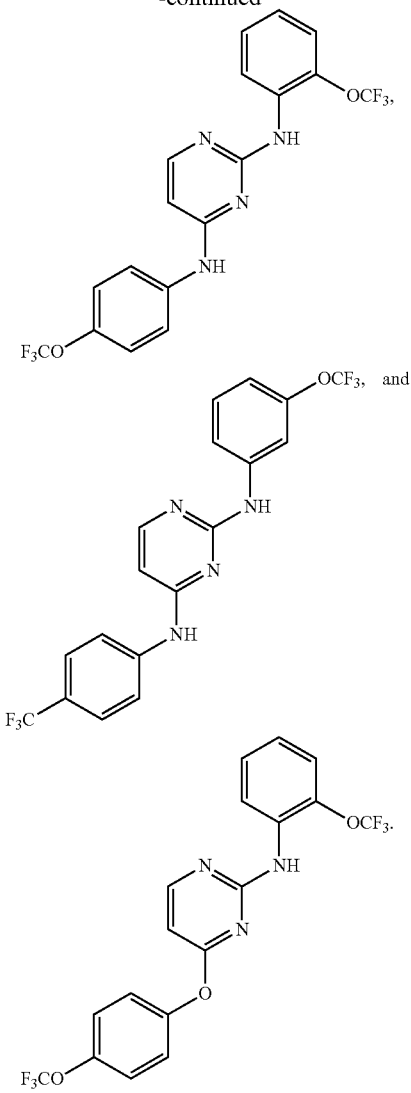

2. A method of inhibiting entry of a virus into a host cell comprising contacting the host cell with an effective amount of a compound of claim 1, wherein the virus is of family Flaviviridae.

3. The method of claim 2, wherein the virus is dengue virus (DENV).

4. A method of treating or preventing a viral infection in a subject comprising administering to the subject an effective amount of a compound of claim 1, wherein the viral infection is a result of a virus of family Flaviviridae.

5. The method of claim 4, wherein the viral infection is a result of dengue virus (DENV).

6. The method of claim 4, wherein the viral infection is selected from the group consisting of: Dengue fever, Japanese encephalitis, Kyasanur Forest disease, Murray Valley encephalitis, St. Louis encephalitis, Tick-borne encephalitis, West Nile encephalitis, Yellow fever, and Hepatitis C.

7. The compound of claim 1, wherein the compound is

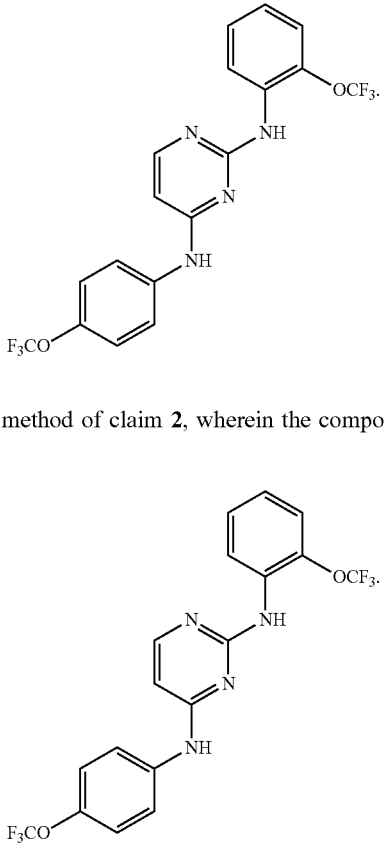

8. The method of claim 2, wherein the compound is

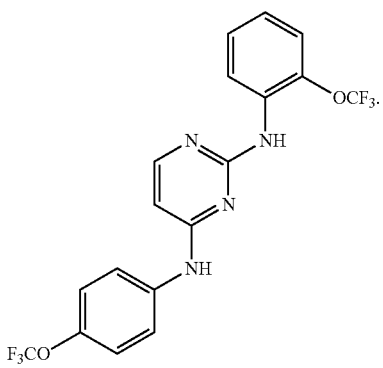 [SMILES: FC(F)(F)Oc1ccc(Nc2ccnc(Nc3ccccc3OC(F)(F)F)n2)cc1]

9. The method of claim 4, wherein the compound is

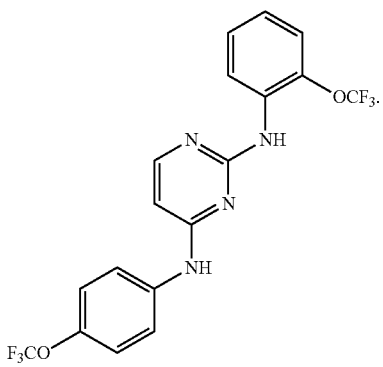 [SMILES: FC(F)(F)Oc1ccc(Nc2ccnc(Nc3ccccc3OC(F)(F)F)n2)cc1]

* * * * *